(12) United States Patent
Lu et al.

(10) Patent No.: US 12,064,012 B2
(45) Date of Patent: Aug. 20, 2024

(54) MULTI-MODAL SENSOR FUSION PLATFORM

(71) Applicant: INTERLINK ELECTRONICS, INC., Irvine, CA (US)

(72) Inventors: Chee Wai Lu, Singapore (SG); Wai Jye Chan, Singapore (SG); Kok Keong Law, Singapore (SG); Cheng Seong Lee, Singapore (SG)

(73) Assignee: INTERLINK ELECTRONICS, INC., Irvine, CA (US)

( * ) Notice: Subject to any disclaimer, the term of this patent is extended or adjusted under 35 U.S.C. 154(b) by 403 days.

(21) Appl. No.: 16/474,873

(22) PCT Filed: Jan. 3, 2018

(86) PCT No.: PCT/US2018/012262
§ 371 (c)(1),
(2) Date: Jun. 28, 2019

(87) PCT Pub. No.: WO2018/129098
PCT Pub. Date: Jul. 12, 2018

(65) Prior Publication Data
US 2019/0335843 A1    Nov. 7, 2019

Related U.S. Application Data

(60) Provisional application No. 62/442,243, filed on Jan. 4, 2017.

(51) Int. Cl.
*A43B 3/34*    (2022.01)
*A43B 7/28*    (2006.01)
(Continued)

(52) U.S. Cl.
CPC ............ *A43B 3/34* (2022.01); *A43B 7/28* (2013.01); *A43B 17/006* (2013.01); *A43D 1/02* (2013.01);
(Continued)

(58) Field of Classification Search
CPC ....... A43B 3/0005; A43B 7/28; A43B 17/006; A43B 17/00; A43D 1/02; A61B 5/1038;
(Continued)

(56) References Cited

U.S. PATENT DOCUMENTS

| 10,070,682 B2 | 9/2018 | Rubin et al. | |
| 2004/0107604 A1* | 6/2004 | Ha | A43B 3/26 36/97 |

(Continued)

FOREIGN PATENT DOCUMENTS

| JP | S60-54403 U | 4/1985 |
| JP | 2011-509710 A | 3/2011 |

(Continued)

OTHER PUBLICATIONS

Japanese Office Action issued in corresponding application No. 2019-536147, dated Oct. 27, 2020.

(Continued)

*Primary Examiner* — Patrick Fernandes
(74) *Attorney, Agent, or Firm* — Maschoff Brennan

(57) ABSTRACT

A system may include a bottom layer and a sensing layer disposed on a first side of the bottom layer. The first sensing layer may include a first sensing element and a second sensing element. The first sensing element and the second sensing element may include one of: a force sensing element, a strain sensing element, a motion sensing element, or an environmental sensing element. The first sensing element and the second sensing element may be of a different type of sensing element. The system may also include a communi- (Continued)

cations interface configured to couple the sensing layer with a host controller.

11 Claims, 22 Drawing Sheets

(51) Int. Cl.
*A43B 17/00* (2006.01)
*A43D 1/02* (2006.01)
*A61B 5/00* (2006.01)
*A61B 5/103* (2006.01)
*A61B 5/11* (2006.01)

(52) U.S. Cl.
CPC .............. *A61B 5/1038* (2013.01); *A61B 5/11* (2013.01); *A61B 5/6807* (2013.01)

(58) Field of Classification Search
CPC ....... A61B 5/11; A61B 5/6807; A61B 5/1036; A61B 5/02438; A61B 5/743; A63B 24/0062; A63B 2220/00; G06F 3/011
See application file for complete search history.

(56) References Cited

U.S. PATENT DOCUMENTS

| | | | | |
|---|---|---|---|---|
| 2006/0254369 | A1* | 11/2006 | Yoon | A61B 5/6804 73/862.041 |
| 2007/0204687 | A1* | 9/2007 | Haselhurst | A43D 1/025 73/172 |
| 2007/0245504 | A1* | 10/2007 | Spector | B33Y 50/00 73/172 |
| 2009/0137933 | A1* | 5/2009 | Lieberman | A61B 5/1117 600/595 |
| 2010/0004566 | A1 | 1/2010 | Son et al. | |
| 2013/0190903 | A1* | 7/2013 | Balakrishnan | A63B 71/06 700/91 |
| 2014/0222173 | A1* | 8/2014 | Giedwoyn | A43B 3/0005 700/91 |
| 2014/0266571 | A1 | 9/2014 | Sharma et al. | |
| 2015/0025816 | A1 | 1/2015 | Ross | |
| 2015/0182844 | A1* | 7/2015 | Jang | A61B 5/112 700/91 |
| 2015/0359457 | A1* | 12/2015 | Blumenthal | G06F 3/011 73/172 |
| 2016/0287937 | A1 | 10/2016 | Fitzgerald et al. | |
| 2016/0299021 | A1 | 10/2016 | Thillainadarajah et al. | |
| 2016/0366266 | A1 | 12/2016 | Chung et al. | |
| 2017/0188950 | A1* | 7/2017 | Gazdag | A43B 3/0005 |

FOREIGN PATENT DOCUMENTS

| | | |
|---|---|---|
| JP | 2015-229100 A | 12/2015 |
| JP | 2016-508787 A | 3/2016 |
| JP | 2016-513997 A | 5/2016 |
| WO | 2012/112938 A2 | 8/2012 |
| WO | 2012/112938 A3 | 8/2012 |

OTHER PUBLICATIONS

European Search Report issued in corresponding application No. 18736398.1, dated Jul. 21, 2020.

Japanese Office Action issued in corresponding application No. 2021-165306 dated Sep. 27, 2022.

JP Office Action dated Mar. 14, 2023 as received in Application No. 2021-165306.

EP Office Action dated Aug. 31, 2023 as received in Application No. 18736398.1.

* cited by examiner

MULTI-MODAL SENSOR FUSION PLATFORM

FIELD

The embodiments discussed herein are related to a multi-modal sensor fusion platform.

BACKGROUND

The internet of things (IoT) typically includes a network of physical devices, vehicles, buildings and other items—embedded with electronics, software, sensors, actuators, and network connectivity that enable these objects to collect and exchange data, often without user input. IoT devices are sometimes referred to as smart devices. Recently, some advances have been made in developing smart insoles for use in shoes. These smart insole solutions, however, rely primarily on force and/or pressure mapping using force sensing elements. Using force sensing elements alone may present various limitations to smart insoles.

The subject matter claimed herein is not limited to embodiments that solve any disadvantages or that operate only in environments such as those described above. Rather, this background is only provided to illustrate one example technology area where at least one embodiment described herein may be practiced.

BRIEF DESCRIPTION OF THE DRAWINGS

Example embodiments will be described and explained with additional specificity and detail through the use of the accompanying drawings in which.

DESCRIPTION OF EMBODIMENTS

Smart insoles are often used for force and/or pressure mapping of a human foot. Conventional smart insole solutions often rely on force and/or pressure mapping using force sensing elements, which typically are integrated within the smart insole as a force sensing layer. Conventional smart insole solutions may provide physical sensing functions that focus on extraction of parameters including feet pressure mapping, walking/running speed and pronation/supination. Under conventional techniques, the force sensing layer size and geometry must exactly match the shoe size and type, otherwise the force sensing elements may not provide accurate readings. Further, force sensing elements are often sensitive to environmental conditions including temperature and humidity, which may change dramatically based on various activities of a user (such as running).

Using force sensing elements alone may present various limitations to smart insoles. For example, a human foot in motion may produce forces in many different directions, which may be difficult to accurately measure in a consistent manner. Further, it may be difficult to measure motion characteristics using force sensing elements alone. For example, while in motion due to external forces (e.g., movement of the user's foot), the insole may experience bending or flexing. Conventional systems may not be able to distinguish or separate these bending or flexing forces from other types of forces. Moreover, conventional systems may not provide real-time physical user feedback based on physiological monitoring parameters and also may not provide intuitive real-time visualization of the physiological monitoring parameters. Further, conventional systems may not allow tracking of the physiological monitoring parameters using a user profile identification. And, conventional systems may not provide a duplex data communication link between sensors and a host device.

Aspects of the present disclosure address these and other shortcomings by providing a system (such as a smart insole or a system that may be positioned inside a shoe) for force/pressure mapping and motion measurement within a smart insole, foot pressure monitoring, shoe customization, and other related applications.

Embodiments of the present disclosure are further described with reference to the accompanying drawings.

Figure 1:
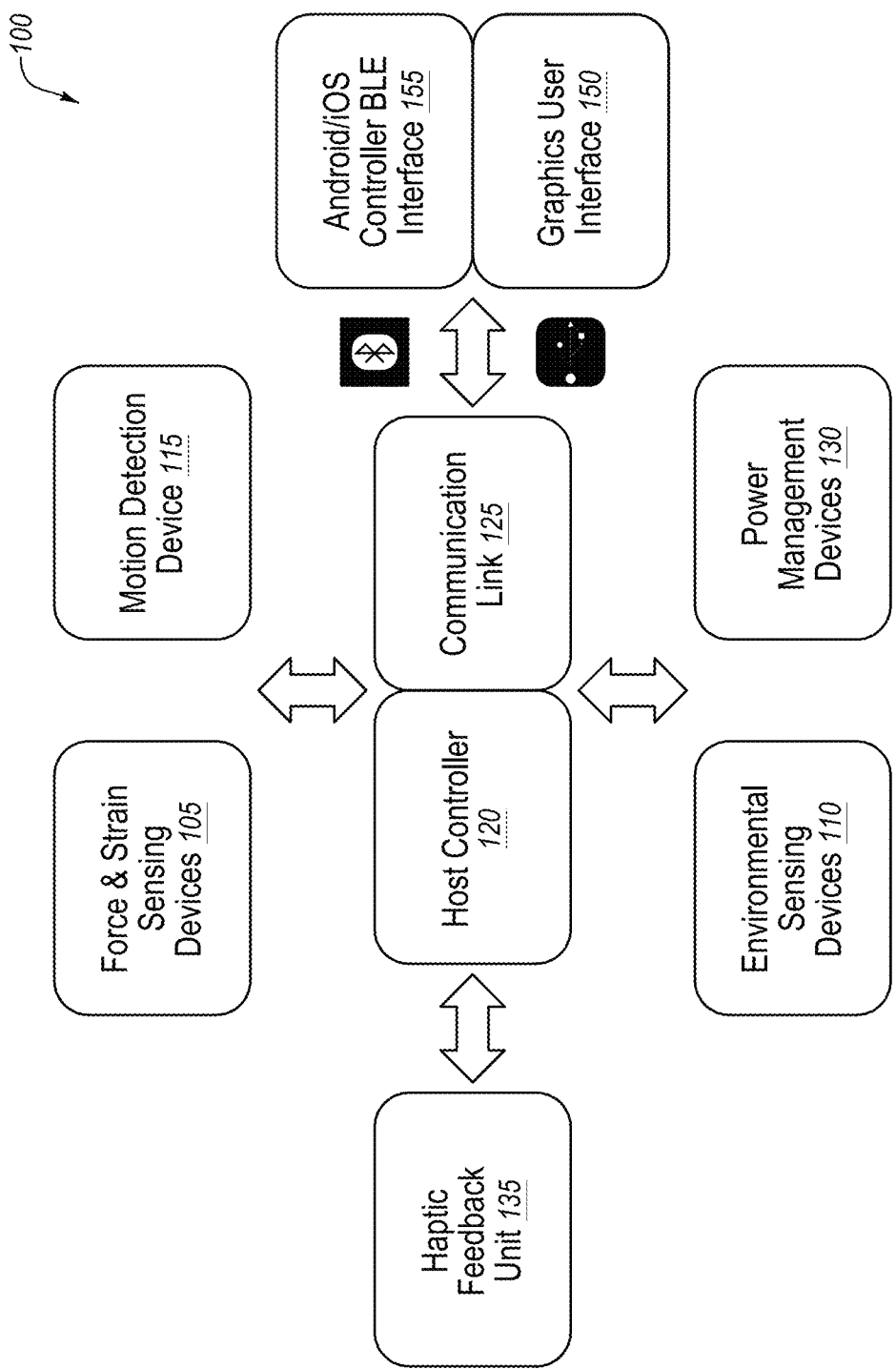
FIG. 1 illustrates an example system diagram of a multi-modal sensor fusion platform.

FIG. 1 illustrates an example multi-modal sensor fusion platform ("system") 100. The system 100 may include various sensors, haptic devices, controllers, interfaces, power management devices, etc.

The system 100 may include one or more strain sensing elements 105 and/or one or more force sensing elements 105. The one or more strain sensing elements 105 may include two-dimensional or three-dimensional strain sensing elements. The one or more force sensing elements may include one or more force/pressure sensors.

In at least one embodiment, the system 100 may include an insole, which may include one or more force sensing elements 105. The one or more force sensing 105 elements may be configured to detect and/or measure foot force and/or pressure distribution across some or all of a surface of the insole. The insole may include one or more strain sensing elements 105. The one or more strain sensing elements 105 may be configured to detect and/or measure bending and/or flexing of the insole.

The insole may include one or more environmental sensing elements 110. The one or more environmental sensing elements 110 may be configured to detect and/or measure environmental parameters including temperature and humidity. At least some of the environmental parameters may contribute to noise in the system. The environmental parameters may be accounted for and/or mathematically reduced, minimized or ignored to reduce the noise in the system. The integration of more than one type of sensing elements in combination with signal processing algorithms may provide a robust force and pressure mapping and motion measurement solution.

The system 100 may also include motion detection devices 115, which may be used to extract the physiological monitoring parameters. The one or more motion detection devices 115 may be configured to detect and/or measure movement, changes in movement, motion, inertia, etc. Example motion detection devices 115 may include an accelerometer, gyroscope, etc. Analysis of the physiological monitoring parameters can be used in a broad range of applications including running performance enhancement, physiotherapy and prevention of injury. Results of data analytics may be shown in the form of quantitative data and charts on a portable device.

In at least one embodiment, the system 100 may include a physical stack-up topology of an insole may include a top insole layer, an interposer, one or more force sensing elements 105, one or more strain sensing elements 105, one or more environmental sensing elements 110, one or more motion sensing elements 115, and a bottom insole layer. The interposer may include an electrical interface routing between a socket or a connection to another. For example, the interposer may connect any of the one or more force sensing elements 105, the one or more strain sensing elements 105, the one or more environmental sensing elements, 110 and/or the one or more motion sensing elements 115 to a host controller 120.

In at least one embodiment, the system 100 may include a physical arrangement of at least two separate sensing systems. The two separate sensing systems may include a toe area/zone system and a heel area/zone system. For example, the toe area/zone system may be sized and configured to fit in a toe area/zone of a shoe. Similarly, the heel area/zone system may be sized and configured to fit in a heel area/zone of a shoe. The two separate sensing systems may enable various configurations for different shoes, sizes, or types, etc. using the same two separate sensing systems. Thus, the same two separate sensing systems may be used to accurately provide force/pressure mapping and motion measurement in different shoes. The two separate sensing systems may be communicatively and/or electrically connected to each other. The two separate sensing systems may be communicatively and/or electrically connected to the host controller 120.

In at least one embodiment, the system 100 may include at least two sensing layers. Each sensing layer may include one or more force sensing elements which may provide dynamic insole force/pressure detection and measurement within each sensing layer. Each sensing layer may also include one or more strain sensing elements and one or more environmental sensing elements.

In at least one embodiment, the system 100 may include multiple force sensing elements 105. Each force sensing element 105 may be individually customized for optimal dynamic force/pressure characteristics including but not limited to force/pressure range, rise time, fall time, etc. Each force sensing element 105 may be assigned a specific location within a shoe, location on an insole, and/or a position on a foot. Each force sensing element 105 may be individually customized to measure dynamic force/pressure characteristics based on the respective location within a shoe, location on an insole or position on the foot. The system 100 may also include multiple strain sensing elements 105, which may provide dynamic insole bending/flexing detection. The system 100 may also include multiple environmental sensing elements 110 which may provide dynamic environmental parameter measurement.

Similarly, in at least one embodiment, the system 100 may include multiple motion sensing elements 115. Each motion sensing element 115 may be individually customized to detect optimal dynamic motion characteristics. Each motion sensing element may be assigned a specific location within a shoe, location on an insole, and/or a position on a foot. Each motion sensing element may be individually customized to measure motion characteristics based on the respective location within a shoe, location on an insole or position on the foot.

In at least one embodiment, the host controller 120 may include a multi-model HMI controller. In at least one embodiment, the host controller 120 may include a processor configured to execute computational processing of dynamic force detection and measurement data from force sensing elements. The processor may use the dynamic force detection and measurement data, for example, to determine a foot force/pressure map across some or all of an insole surface or along the bottom of a user's foot. The processor may also be configured to execute computational processing of dynamic strain detection and measurement data from strain sensing elements. The processor may use the dynamic strain detection and measurement data to determine foot flexing characteristics. The processor may also be configured to execute computational processing of dynamic environmental sensing data received from one or more environmental sensing elements. The processor may also use the environmental sensing data to achieve dynamic environmental compensation of force sensing elements and the strain sensing elements. The processor may also be configured to execute computational processing of dynamic motion sensing data received from one or more motion sensing elements. The processor may also use the motion sensing data to achieve dynamic motion compensation of force sensing elements, the strain sensing elements and/or the environmental sensing elements. The host controller may also include an embedded host controller. The host controller may include circuitry configured to receive data from the sensing elements. The host controller may include a memory to store the data and a processor to execute operations.

The host controller may be electronically connected to a client device via a communication link 125. In at least one embodiment, the sensor may be coupled to the client device via a wired communication link. The communication link may provide any form of wired or wireless communication capability between the system and any other device. In some embodiments, the communication link may include a radio frequency (RF) antenna. By way of example and not limitation, the communication link may be configured to provide, via wireless mechanisms, LAN connectivity, Bluetooth connectivity, Bluetooth Low Energy (BLE), Wi-Fi connectivity, NFC connectivity, M2M connectivity, D2D connectivity, GSM connectivity, 3G connectivity, 4G connectivity, LTE connectivity, any other suitable communication capability, or any suitable combination thereof. The insole may include any number of communication links. The communication link may provide various interface 155 functionality, such as an Android®/iOS® controller and display module, game engine visualization, various modes (e.g., walking and running modes), a Bluetooth Low Energy Interface, etc.

In at least one embodiment, the host controller 120 (e.g., the processor) may scan the sensing elements (e.g., the force sensing elements 105, strain sensing elements 105, the environmental sensing elements 110, the motion sensing elements 115). The processor may scan the sensing elements periodically. In at least one embodiment, the processor may use a variable scanning rate for at least some of the sensing elements, which may provide a benefit of optimal data resolution and/or power consumption. For example, some areas of a user's foot may move more frequently, or may experience a greater rate of change in force or pressure as compared to other areas of the user's foot. These areas may be scanned more frequently for higher data resolution. Those areas with lesser rate of change in force or pressure may be scanned less frequently, which may reduce power consumption of the system 100.

The processor may perform various analyses based on data received from the sensing elements (and from any other sensors, as described herein). For example, the processor may generate a force and/or pressure map of a human foot. The force and/or pressure map may be an instantaneous snapshot of the current state of the human foot. The force and/or pressure map may also include data over time and the map may represent average, median, or other values. The map may be used to determine a level of pronation (e.g., overpronation, underpronation, supination). The map may be viewable as a "heat map" which may show force or pressure ranges in different colors. In at least one embodiment, the processor may send the sensor data to another device (e.g., a server, a client device) for processing. The processor may also send the sensor data to another portable or wearable device such as smartphone or smartwatch.

The system 100 may also include a power management device 130 which may provide and/or regulate power for the system 100.

The system 100 may also include a haptic feedback unit 135 that may drive haptic feedback to the system. For example, the host controller 120 may receive sensor data from the sensing array (e.g., any of the sensors 105, 110, 115). Based on the sensor data, the host controller 120 may generate and send instructions to the haptic feedback unit 135 to produce a haptic response via the system 100 (e.g., as a haptic feedback via an insole that the user may feel in their foot). The haptic response may be provided via a haptic device via the insole that may be felt by the user. Example haptic response may include, but are not limited to, a press, a pulse, a shock, a release, all of which may be short, long, or repeated. The haptic response may be used to encourage a particular behavior. For example, if a runner favors his heels, the haptic response may notify or remind the user when the user is favoring his heels. The user may then adjust his running technique toward his toes and away from his heels.

Systems and method described herein may be used in myriad applications, such as with shoes, insoles, smart sensing mats, flooring, recreational equipment, or other gym or exercise related applications.

Figure 2:
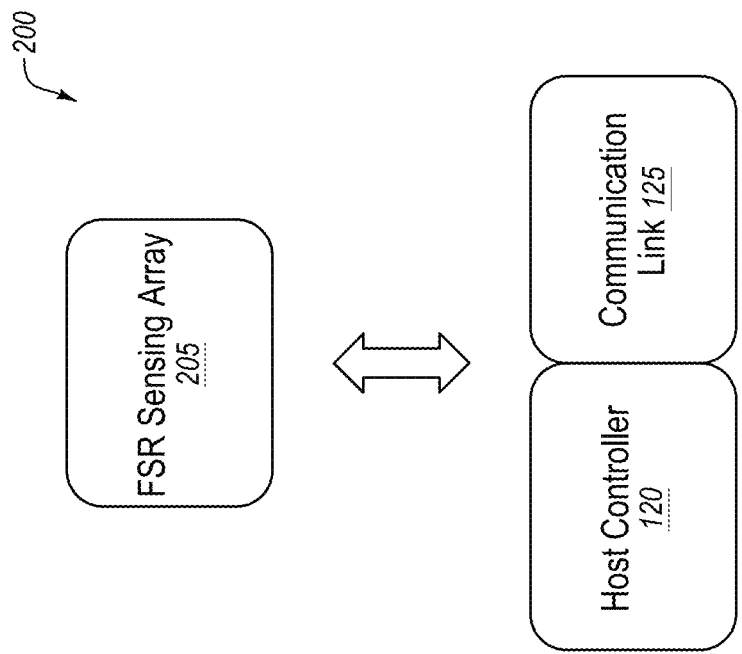
FIG. 2 illustrates an arrangement of an example smart shoe system for sensing various characteristics relating to a human foot and/or a shoe.

FIG. 2 illustrates an arrangement of an example smart shoe system 200 for sensing various characteristics relating to a human foot and/or a shoe. The example smart shoe system may include some or all of the components of the system of FIG. 1. For example, the smart shoe system 200 may include one or more force sensing elements 105, one or more strain sensing elements 105, one or more environmental sensing elements 110, one or more motion sensing elements 115), which may collectively be referred to as a FSR sensing array 205. The FSR sensing array 205 may be scalable and/or adjustable between shoe sizes. For example, a first FSR sensing array 205 may be adjustable between shoes sizes 6 to 9. The FSR sensing array 205 may include any number of sensors. In an example, the FSR sensing array 205 may include 20 or more sensor nodes.

The host controller 120 may measure approximately 5 cm×5 cm×1 cm. The host controller 120 may include logic for determining pressure mapping and/or motion control based on readings from the FSR sensing array 205. The host controller 120 may also be coupled to a communication link 125. The host controller 120 may also be coupled to another controller, such as an Android® controller and display module, which may be configured for game engine visualization. Using the other controller, motion and movement detected by the FSR sensing array 205 may be translated into movement of an avatar of a user or a digital character.

Figure 3:
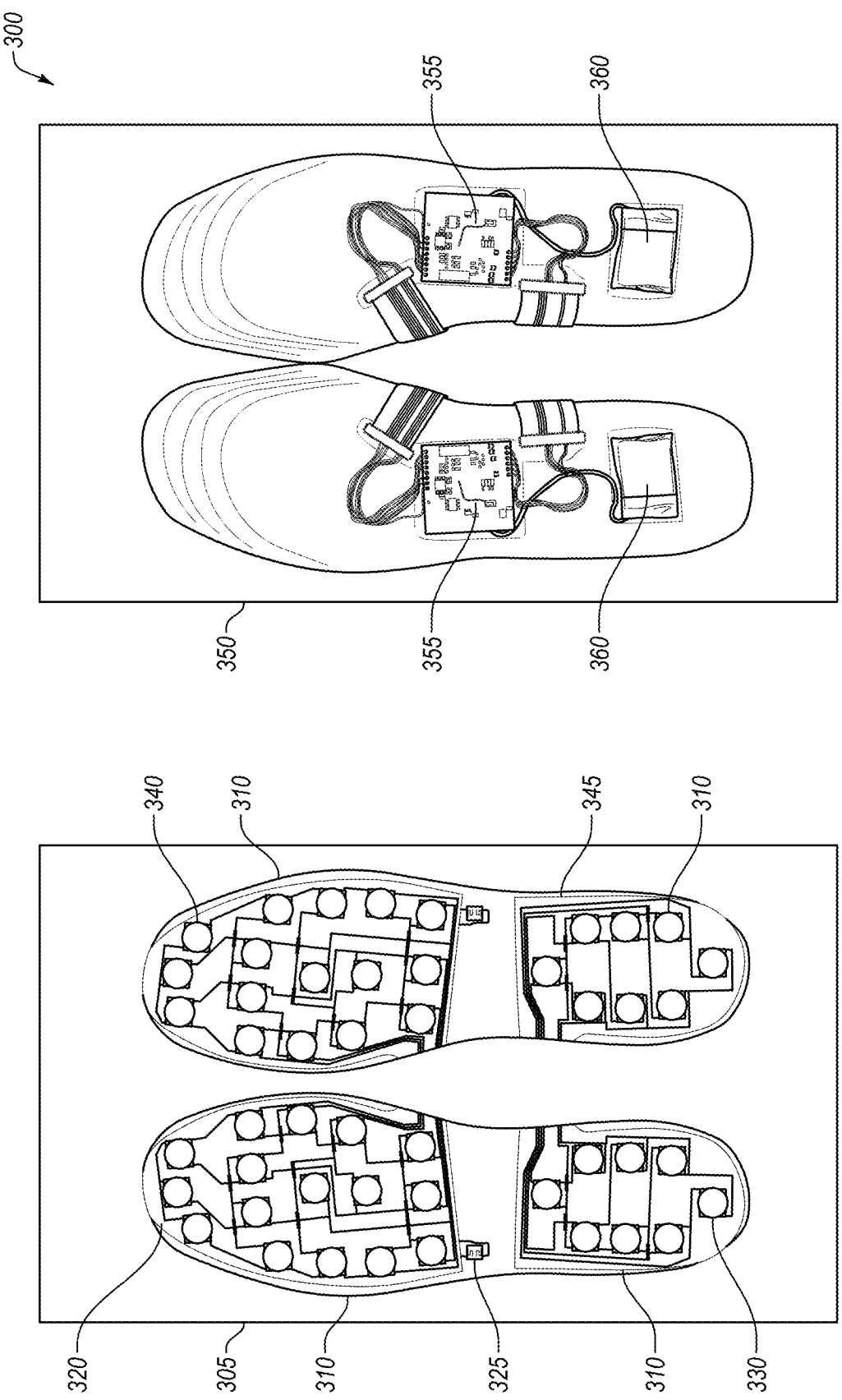
FIG. 3 illustrates an arrangement of an example system for sensing various characteristics relating to a human foot and/or a shoe.

FIG. 3 illustrates an arrangement of an example system for sensing various characteristics relating to a human foot and/or a shoe. The left side of FIG. 3 may illustrate a first view 305 of the system, where sensing elements may be closer to an object to measure (e.g., a foot). The right side of FIG. 3 may illustrate a second view 350 of the system illustrating a circuit board 355, power supply (e.g., battery) 360, etc. may be coupled to the system.

The system 300 may include sensing elements 310 that may be configured to measure force, strain, motion, movement, and other environmental characteristics exerted by a foot or a shoe. The system 300 may include an insole that may be removably inserted within a shoe. Alternatively, the insole may be embedded within or attached to a shoe. As illustrated, the insole may include a top insole layer 320, an interposer 325, one or more sensing elements 310 coupled to the interposer 325, and a bottom insole layer 330.

The top insole layer 320 may be shaped to fit within a shoe, boot, sandal, or any other type of footwear. The top insole layer 320 may be formed from any material or combination of materials. Similarly, the bottom insole layer 330 may be formed from any material or combination of materials. The material may include a porous material, foam material, plastic material, or any other natural or synthetic material. The top insole layer 320 may be composed of different material or materials as the bottom insole layer 330. The bottom insole layer 330 may be formed from a stiffer material or an aggregate stiffness of the bottom insole layer may be stiffer than the top insole layer 320. In at least one embodiment, the bottom insole layer 330 may provide a rigid/stable base for the interposer 325 and/or the sensing elements 310. The top insole layer 320 may be attached to the interposer 325, such as by being bonded (e.g., glued, welded, sewed, etc.) to the interposer 325. In at least one embodiment, the bottom insole layer 330 may be formed from a resilient material configured to withstand repeated impact with a hard surface (e.g., concrete). In at least one embodiment, the bottom insole layer 330 may include or be part of a sole of a shoe.

Additionally or alternatively, the interposer 325 may be connected to an external circuit board (not illustrated in FIG. 3) as part of the external host controller. The interposer may also include or be part of any type of circuit board. The circuit board may be formed from any material. The circuit board may be rigid or flexible.

One or more sensing elements 210 may be coupled to the interposer. The one or more sensing elements 210 may be referred to as a sensing array. The one or more sensing elements 210 may include one or more force sensing elements, one or more strain sensing elements, one or more motion sensing elements, and/or one or more environmental sensing elements. The one or more strain sensing elements may include one or more two-dimensional strain sensing elements. The sensing elements may be spatially distributed on the interposer. One or more of the sensing elements may be a discrete part that is coupled to the interposer. Alternatively, one or more of the sensing elements may be directly formed, etched, deposited, or printed etc. onto the interposer. For example, a sensing element may be printed on a flexible circuit board (i.e., flex).

As illustrated on the left side 305 of FIG. 3, an example system may include two sensing arrays 340, 345 (e.g., a top and bottom, a toe area and a heel area, etc.). Each sensing array 340, 345 may include one or more force sensing elements 310 which may provide dynamic insole force/pressure detection and measurement within each sensing layer. Each sensing array 340, 345 may also include one or more strain sensing elements and one or more environmental sensing elements. As discussed above, each sensing array may include a toe area/zone array and a heel area/zone array.

The system 300 may also include a controller, as further described in conjunction with FIG. 1. The controller may include circuitry configured to receive data from the sensing elements 310. The controller may include a memory to store the data and a processor to execute operations. The controller may include a communication link.

The controller may perform various analyses based on data received from the sensing elements (and from any other sensors, as described herein). For example, the controller may generate a force, motion, and/or pressure map of a human foot. The force and/or pressure map may be an instantaneous snapshot of the current state of the human foot. The force and/or pressure map may also include data over time and the map may represent average, median, or other values. The map may be used to determine a level of pronation (e.g., overpronation, underpronation, supination). The map may be viewable as a "heat map" which may show force or pressure ranges in different colors. In at least one embodiment, the controller may send the sensor data to another device (e.g., a server, a client device) for processing. The controller may also send the sensor data to another portable or wearable device such as smartphone or smartwatch.

The insole may include any number of sensors. The sensor may represent any hardware or software sensor capable to detect any characteristic of or near the insole (such as data indicative of motion or environment), including but not limited to an accelerometer, gyroscope, altimeter, global positioning system (GPS), pedometer, magnetometer, a thermometer, a humidity sensor, a barometric pressure sensor, a GPS receiver, any other sensor that may detect motion, environmental, or human state, or any combination thereof. Any motion detected by the sensor may be referred to as a motion characteristic. The sensor may detect various motion patterns that may be associated with a particular movement of a human. The sensor may include any suitable system, apparatus, device, or routine capable of detecting or determining one or more of the following: tilt, shake, rotation, swing, and any other motion. For example, the sensor may detect that the insole is periodically moving in a circular manner that is indicative of a tracked individual taking steps (e.g., walking, running). In some embodiments, the sensor may be configured to detect or determine a location of a particular tracked individual. For example, the sensor may include a GPS receiver, a Wi-Fi signal detector, a mobile phone communication network signal detector, a Bluetooth beacon detector, an Internet Protocol (IP) address detector or any other system, apparatus, device, or module that may detect or determine a location of the particular tracked individual. The location may include one or more labels or designations (e.g., home, work, gym). In some embodiments, the sensor may be an integrated sensor that includes two or more different sensors integrated together. For example, the sensor may be an integrated sensor that combines a three-dimensional (3D) accelerometer, a 3D gyroscope, and a 3D magnetometer.

The insole may also include any number of activity trackers. An activity tracker may represent any hardware or software sensor or device that may be used to detect characteristics (or data indicative of the characteristics) of a tracked individual who is using the insole, including but not limited to, a heart rate monitor, a blood pressure monitor, thermometer, moisture sensor, respiration sensor, electrodermal activity sensor, sleep sensor, etc. The activity tracker may be used to identify characteristics of the tracked individual who is using the insole. In some embodiments, the heart rate monitor may be configured to measure or determine heart rate or indicators of heart rate. For example, the heart rate monitor may include one or more sensors (e.g., a photoresistor or a photodiode or the like) configured to detect a pulse, a skin temperature, etc. of a monitored tracked individual.

In these or other embodiments, the activity tracker may include a heart rate monitor may include one or more systems, apparatuses, devices, or modules configured to determine the heart rate based on the detected indicators. In some embodiments, an occurrence in a life of the particular tracked individual may include a heart rate of the particular tracked individual, a heart rate maintained by the particular tracked individual for a particular amount of time, a heart rate recovery time, etc., which may be determined by the host controller (or by an external computing device) based on data received from one or more heart rate monitors or from other activity trackers or sensors.

The insole may also include any number of haptic feedback devices that may provide any type of haptic feedback to the user.

The insole may include more or fewer features. For example, the insole may not include a top insole layer and the sensing elements may be disposed such that an outward facing surface of each sensing element may be substantially coplanar with a foot-facing surface of the interposer. In such an embodiment, the interposer may be formed from a material that may provide some degree of comfort to a human foot. The interposer, for example, may be formed from a pliable material. In at least one embodiment, the interposer may include one or more recesses in which the sensing elements may be affixed.

As discussed above, in at least one embodiment, the left side 305 of FIG. 3 illustrates an example system that includes two sensing arrays. A first sensing array may be shaped to fit in a first portion of a shoe (e.g., a portion near where a user would place their toes) and a second sensing array may be shaped to fit in a second portion of the shoe (e.g., a portion near where a user would place their heel). Each of the first sensing array and the second sensing array may include any number of sensing elements. As illustrated, the first sensing array includes a strain sensing element, multiple force sensing elements and multiple environmental sensing elements. As illustrated, the second sensing array includes multiple force sensing elements and multiple environmental sensing elements. The sensing array and the second sensing array may be independently communicatively and/or electronically coupled to a host controller (e.g., the host controller of FIG. 1) via a connector interface. In at least one embodiment, the first sensing array and the second sensing array are communicatively and/or electronically coupled to each other via respective connector interfaces, such as via a flexible printed circuit with a connector. In such an embodiment, either the first sensing array or the second sensing array may be communicatively and/or electronically coupled to the host controller via a connector interface.

The arrangement of two sensing arrays enables reconfiguration of shoe length or size. Additionally, force sensing elements may be located in regions where higher levels of force/pressure may be applied by the foot. Strain sensing elements (e.g., two dimensional strain sensing elements) may be located in regions where higher levels of bending/flexing may be applied by the foot. Environmental sensing elements may be located in regions where there may be minimal levels of force/pressure or bending/flexing but subjected to equivalent environmental parameters as the force sensing and two-dimensional strain sensing elements.

In an example, the system may be used for dynamic motion monitoring in physiotherapy where the goal would be for the user to be able to walk correctly after medical treatment. In another example, the system may be used for dynamic motion monitoring in sports (e.g., track and field) where the user would be able to improve running performance based on the dynamic motion monitoring both in real time and over time. In some embodiments, haptic devices that may provide haptic feedback may be incorporated into the system to stimulate correct behavior.

Figure 4:
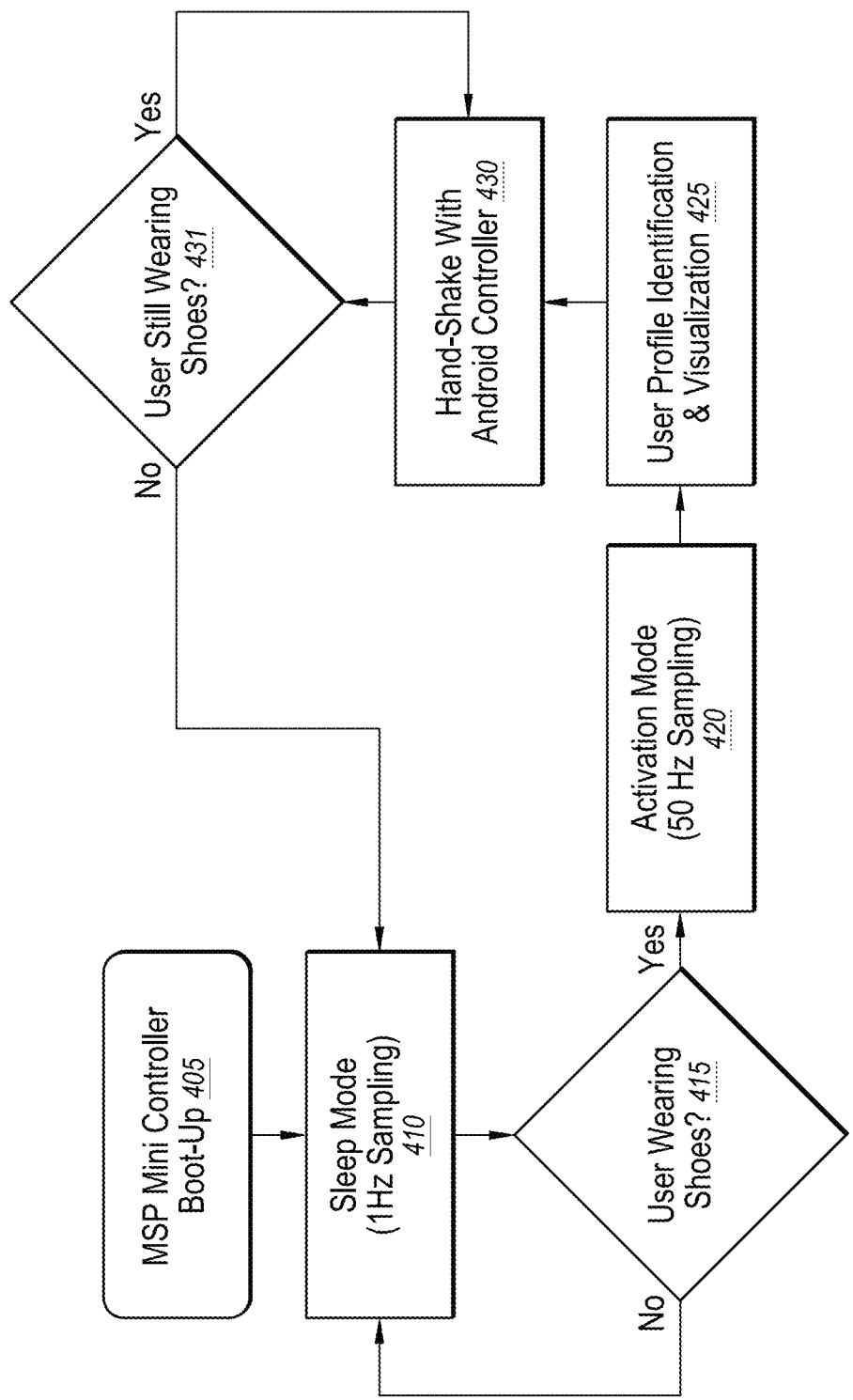
FIG. 4 illustrates an example computational processing flow of a method for determining various functions including but not limited to foot force/pressure mapping and biomechanics such as foot flexing characteristics, such as during walking or running motion.

FIG. 4 illustrates an example computational processing flow of a method 400 for determining various functions including but not limited to foot force/pressure mapping and biomechanics such as foot flexing characteristics, such as during walking or running motion. These functions may be obtained by analysis of measurement data from force sensing elements, dimensional strain sensing elements, motion sensing elements, and environmental sensing elements or other sensors or activity trackers.

The processing flow may be used to self-trigger a smart shoe. The processing flow may be performed by processing logic that may include hardware (circuitry, dedicated logic, etc.), software (such as is run on a general purpose computer system or a dedicated machine), or a combination of both, which processing logic may be included in the system of FIG. 1, or another computer system or device. However, another system, or combination of systems, may be used to perform the methods. For simplicity of explanation, methods described herein are depicted and described as a series of acts. However, acts in accordance with this disclosure may occur in various orders and/or concurrently, and with other acts not presented and described herein. Further, not all illustrated acts may be used to implement the methods in accordance with the disclosed subject matter. In addition, those skilled in the art will understand and appreciate that the methods may alternatively be represented as a series of interrelated states via a state diagram or events. Additionally, the methods disclosed in this specification are capable of being stored on an article of manufacture, such as a non-transitory computer-readable medium, to facilitate transporting and transferring such methods to computing devices. The term article of manufacture, as used herein, is intended to encompass a computer program accessible from any computer-readable device or storage media. Although illustrated as discrete blocks, various blocks may be divided into additional blocks, combined into fewer blocks, or eliminated, depending on the desired implementation.

The method 400 may begin at block 405 where the processing logic may boot a controller. The processing logic may enter a sleep mode at block 410, which may include 1 Hz sampling. At block 415, the processing logic may determine whether a user is wearing a shoe by identifying data from one or more sensing elements and determining whether the identified data matches a profile that indicates that a user is wearing the shoe. If the user is not wearing the shoe ("NO" at block 415), then the processing logic may enter the sleep mode at block 410 for a predetermined amount of time.

If the user is wearing the shoe ("YES" at block 415), then the processing logic may enter an activation mode at block 420, which may include 50 Hz sampling. The processing logic may obtain data from one or more sensing elements, as described herein. For example, the processing logic may obtain force data and motion data of a user's foot while the user moves.

At block 430, the processing logic may identify a user profile associated with the user. In at least one embodiment, at block 430, the processing logic may pair with another device (e.g., a mobile device, wearable, smart watch, etc.) to identify the user profile. To do so, the processing logic may initiate a hand-shake with a remote controller (e.g., an Android® controller, an iOS™ controller, etc.) and may obtain and/or request the user profile. The processing logic may also use the data obtained from the one or more sensing elements to generate a visualization of the data (e.g., via a graphical user interface).

At block 435, the processing logic may determine whether the user is still wearing the shoe by identifying data from the one or more sensing elements and determining whether the identified data matches a data profile that indicates that a user is wearing the shoe. If the user is not still wearing the shoe ("NO" at block 435), then the processing logic may enter the sleep mode at block 410 for a predetermined amount of time. If the user is still wearing the shoe ("YES" at block 435), then the processing logic may initiate or check a handshake with the remote device at block 430.

Figure 5:
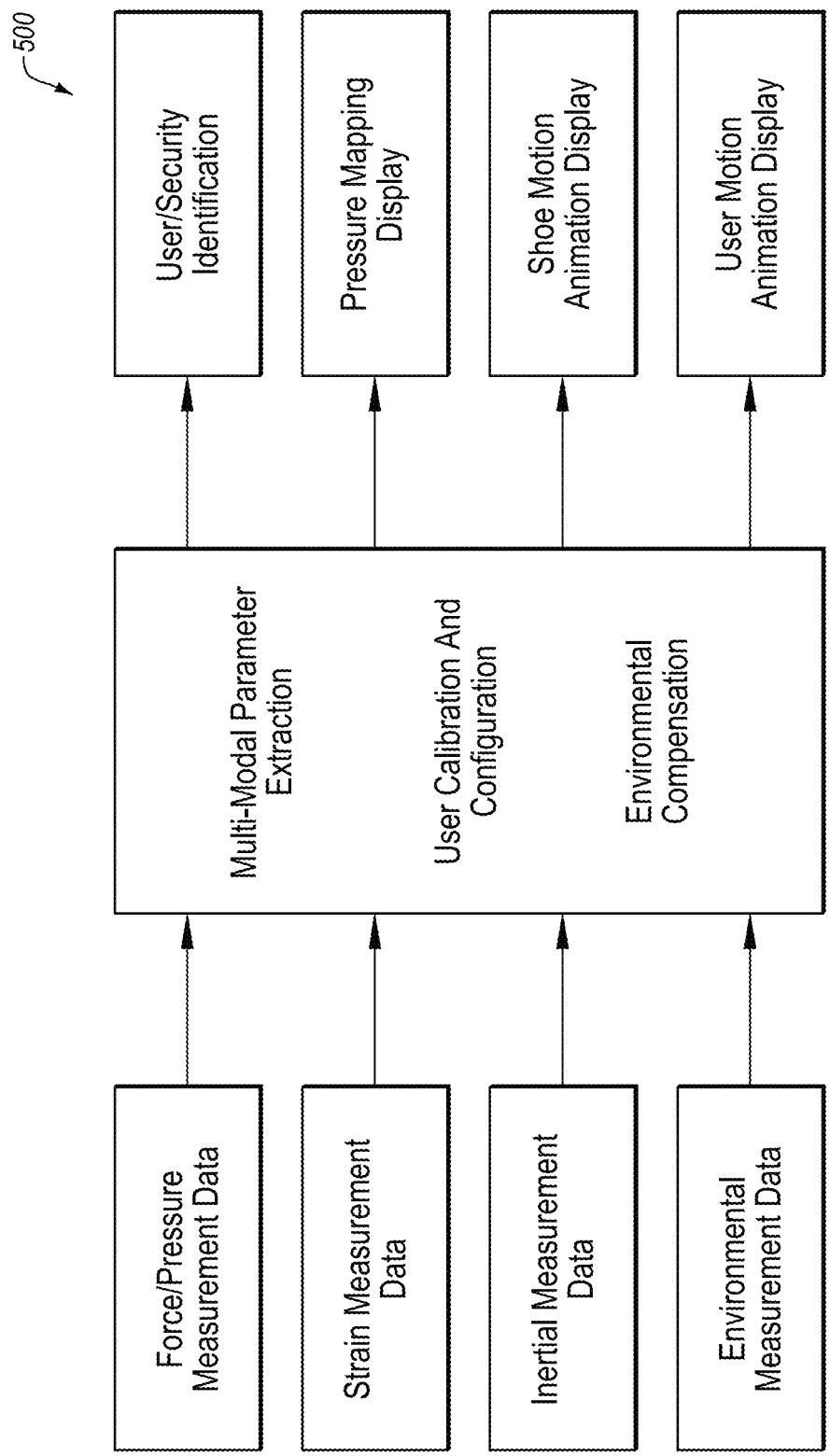
FIG. 5 illustrates an example computational processing flow for determining various functions including but not limited to foot force/pressure mapping and biomechanics such as foot flexing characteristics, such as during walking, running, turning or jumping motion.

FIG. 5 illustrates an example computational processing flow 500 for determining various functions including but not limited to foot force/pressure mapping and biomechanics such as foot flexing characteristics, such as during walking, running, turning or jumping motion. These functions may be obtained by analysis of measurement data from force sensing elements, dimensional strain sensing elements, motion sensing elements, and environmental sensing elements or other sensors or activity trackers. This approach of multi-sensor fusion enables the system to detect specific signatures for multiple types of human motion.

As illustrated, force/pressure measurement data, strain measurement data, inertial (e.g., motion) measurement data, and/or environmental measurement data may be used for multi-modal parameter extraction, user calibration and configuration and environmental compensation. All sensors may have some form of temperature dependence and environmental measurement data allows the temperature dependence to be compensated in different environmental/weather conditions. Different users have different weight and different motion signatures. User calibration allows the system to detect motion profiles correctly. Further, these data and modeling may be used for user/security identification, pressure mapping display, shoe motion animation display (e.g., for virtual reality, augmented reality), and/or user motion animation display.

Figure 6:
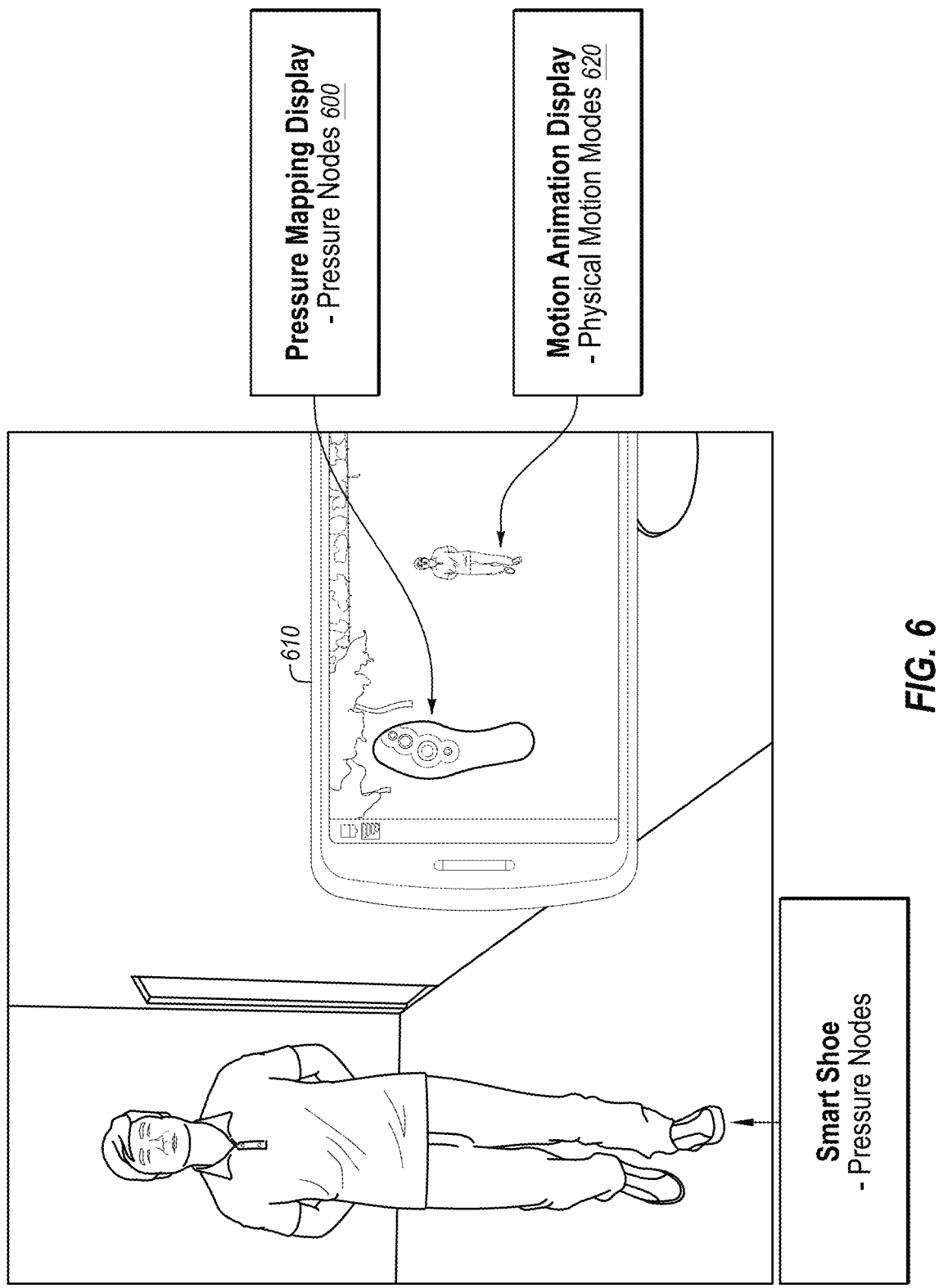
FIG. 6 illustrates an example implementation of a smart shoe system, where the smart shoe includes one or more sensing elements.

FIG. 6 illustrates an example implementation of a smart shoe system 600, where the smart shoe includes one or more sensing elements (e.g., pressure measurement nodes). In at least one embodiment, the smart shoe includes the insoles of FIG. 3. An embedded controller on the smart shoe or in a mobile device may use data received from the one or more sensing elements to generate a pressure mapping display. As illustrated in FIG. 6, the pressure mapping display 600 is presented in a user interface of a mobile device 610. The pressure mapping display 600 may include a color coded "heat map" that indicates various levels of pressure.

The embedded controller on the smart shoe or in the mobile device may also use the data received from the one or more sensing elements to generate a motion animation display 620. The motion animation display 620 may include an avatar that may move similarly to the person wearing the smart shoes. In at least one embodiment, the person's movement is substantially mirrored by the avatar in the motion animation display 620. For example, when the uses leans left, the insole may detect the left lean and may send a corresponding signal to be generated for the motion animation display 620. In this example, the motion animation display 620 would include an avatar that leans left in a similar manner as the user who is wearing the insole(s).

Figure 7:
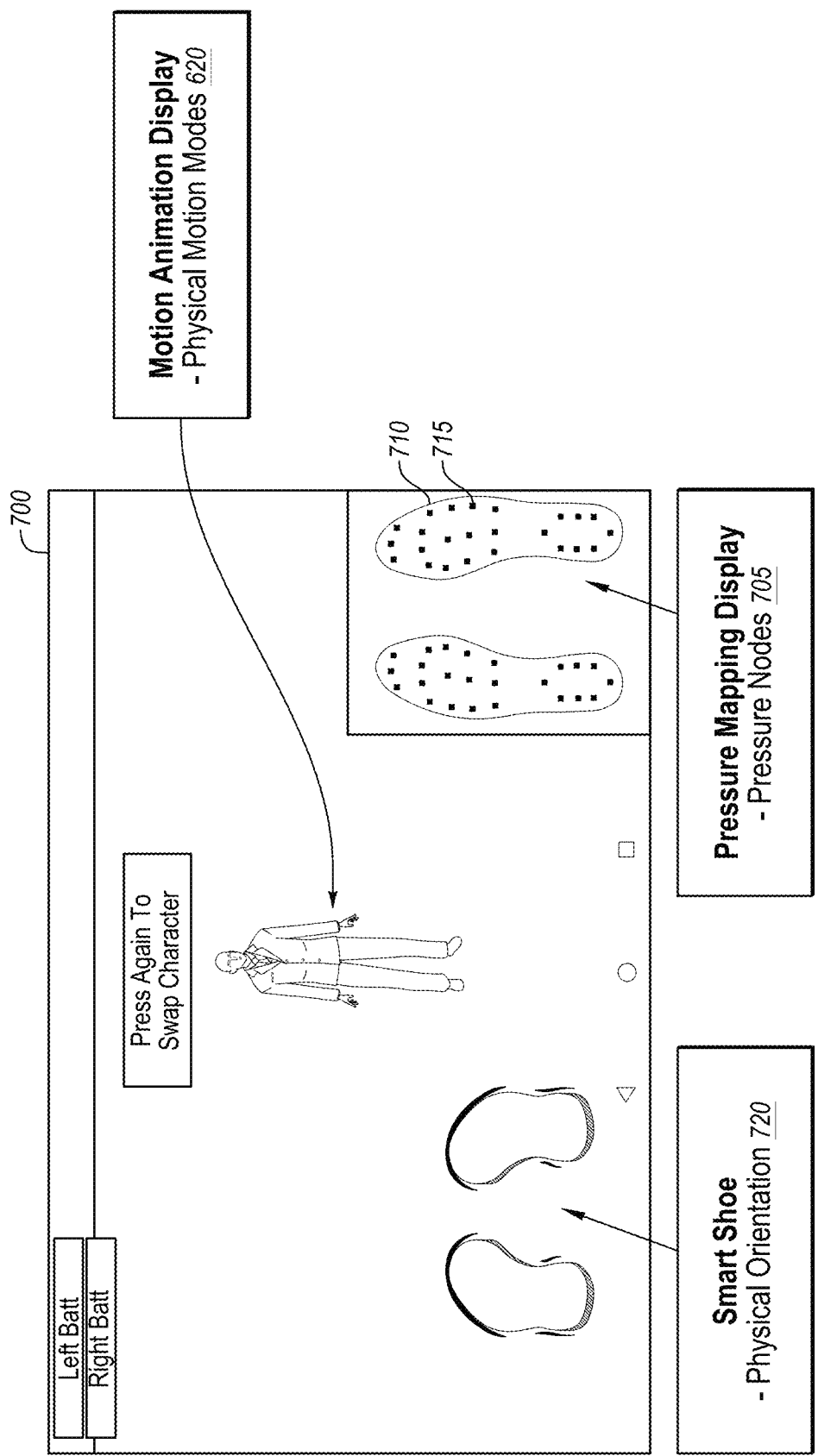
FIG. 7 illustrates an example of a graphical user interface (GUI) for parameter monitoring such as foot/pressure mapping based on measurement data from force sensing elements.

FIG. 7 illustrates an example of a graphical user interface (GUI) 700 for parameter monitoring such as foot/pressure mapping based on measurement data from force sensing elements from any of the systems described.

In at least one embodiment, the GUI 700 may include a pressure mapping display 705 may include an outline of one or more feet 710. The GUI 700 may also include graphical representations of each sensing element (hereafter graphical sensor 715. A sensed value (e.g., a force value) may be represented in each respective sensing element. As illustrated, each graphical sensor is shaded according to its respective force value. The shading may be color based, pattern based, etc. Also illustrated, each graphical sensor includes a respective force reading. The force readings may be an absolute value (e.g., in Newtons or kg·m/s2) or a relative value.

The GUI 700 may also include other portions that may illustrate a physical orientation 720 of a smart shoe, as currently worn by a person. The GUI may also provide a motion animation display 620, as described above.

Figure 8:
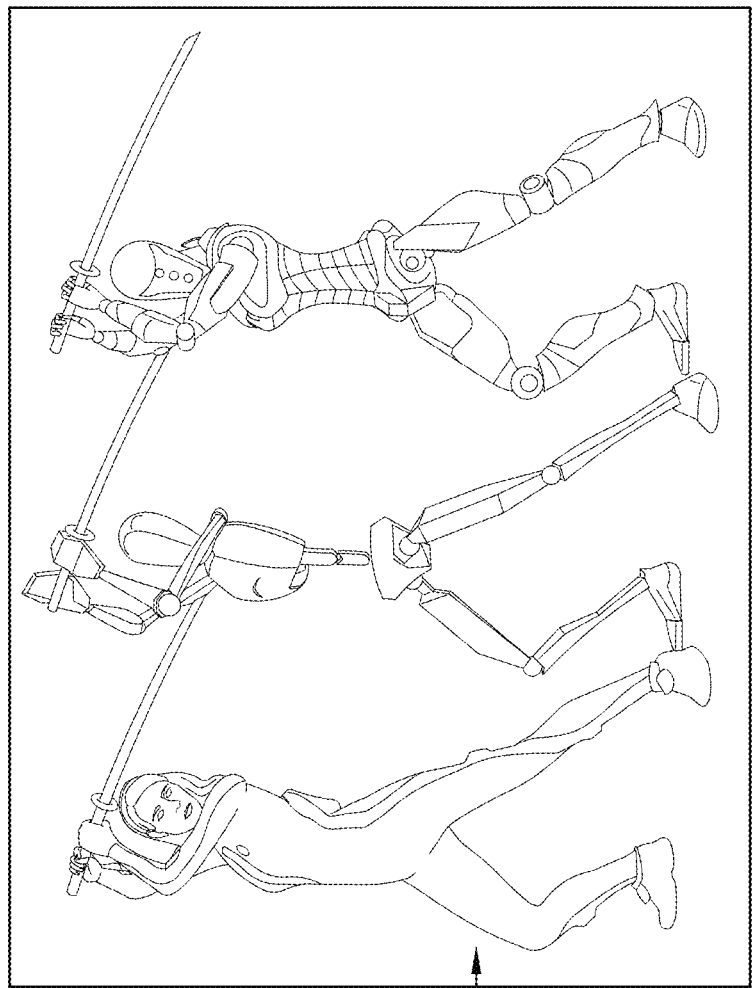
FIG. 8 illustrates various motion animation displays that may be generated based at least in part on measurements obtained from the one or more sensing elements, as described herein.

FIG. 8 illustrates various motion animation displays 800 that may be generated based at least in part on measurements obtained from the one or more sensing elements, as described herein.

Figure 9:
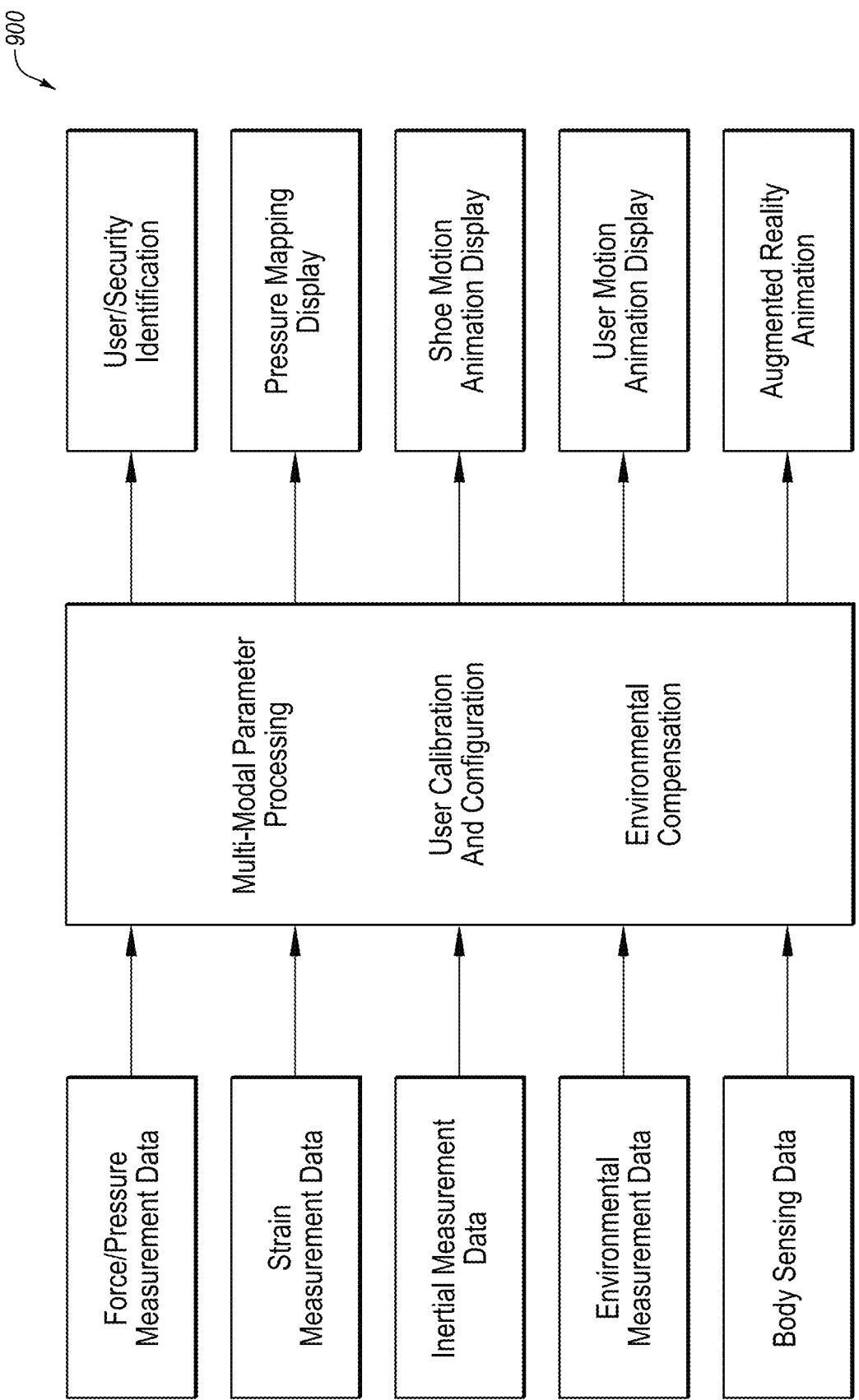
FIG. 9 illustrates an example computational processing flow for determining various functions including but not limited to user profile identification and visualization.

FIG. 9 illustrates an example computational processing flow 900 for determining various functions including but not limited to user profile identification and visualization. These functions may be obtained by analysis of measurement data from force sensing elements, dimensional strain sensing elements, motion sensing elements, environmental sensing elements, body sensing elements, or other sensors or activity trackers. This approach enables expanded multi-sensor fusion by including wearable sensors on the body or arm.

As illustrated, force/pressure measurement data, strain measurement data, inertial (e.g., motion) measurement data, environmental measurement data, and/or body sensing data may be used for multi-modal parameter processing, user calibration and configuration and environmental compensation. Further, these data and modeling may be used for user/security identification, pressure mapping display, shoe motion animation display (e.g., for virtual reality, augmented reality), and/or user motion animation display. The expanded multi-sensor fusion also enables a more detailed user motion animation display in augmented reality.

Figure 10:
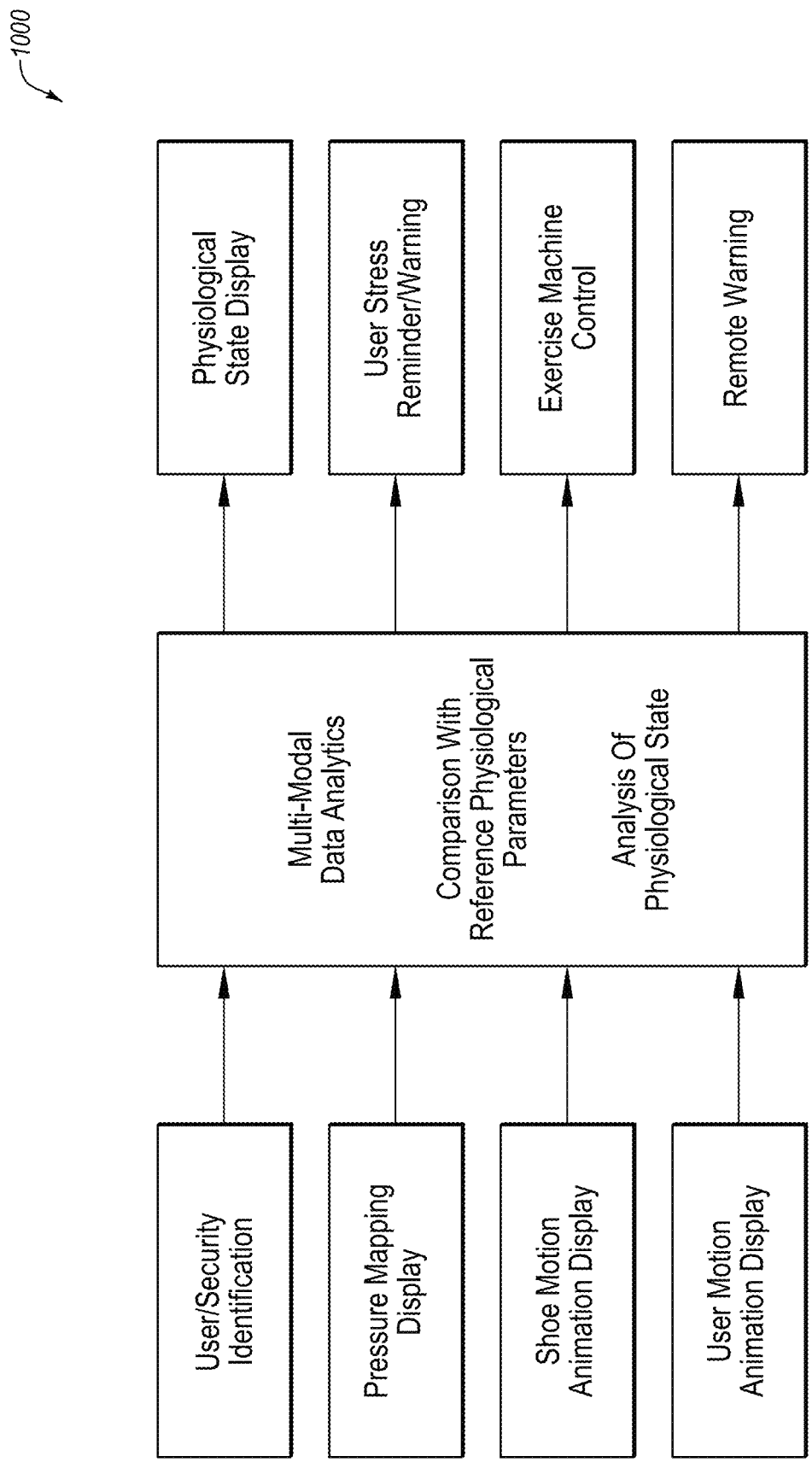
FIG. 10 illustrates an example computational processing flow for determining various functions including but not limited to application of a smart shoe in fitness and/or physiological monitoring.
Figure 11:
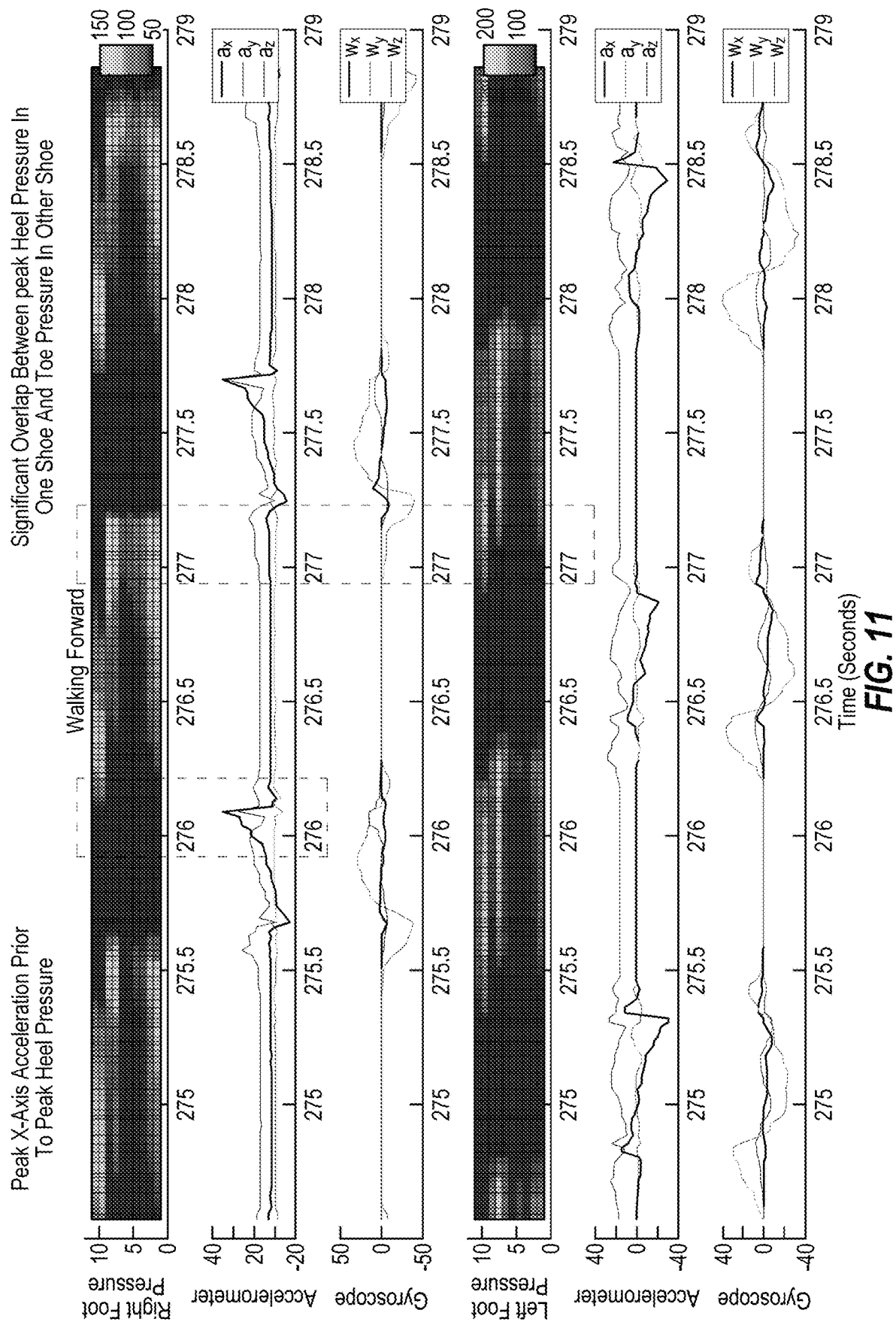
FIGS. 11-21 indicate an example of real-time measurement of monitoring parameters for six defined motion states.

FIG. 10 illustrates an example computational processing flow 1000 for determining various functions including but not limited to application of a smart shoe in fitness and/or physiological monitoring. These functions may be obtained by analysis of measurement data from force sensing elements, motion sensing elements, environmental sensing elements, body sensing elements, or other sensors or activity trackers.

As illustrated, user/security identification, pressure mapping display, shoe motion animation display, and/or user motion animation display may be used may be used for multi-modal data analytics, a comparison with reference physiological parameters, and/or an analysis of physiological state. Further, these data and modeling may be used for physiological state display, user stress reminders and/or warnings, exercise machine goal tracking, and/or a remote warning.

For example, FIG. 10 may illustrate functions in an application example where a user is wearing a smart shoe while running on a treadmill. The user may set the parameters of the treadmill at the beginning of the exercise and adjust the parameters during the exercise, i.e. a highly manual process. In this example, the smart shoe interface is wirelessly connected to the treadmill. The system implementation provides several functions, such as data analytics of multi-sensor parameters, comparison with reference physiological parameters, analysis of physiological state, display of physiological state, provide stress reminder/warning to the user if the treadmill parameters settings are excessive (speed is too fast, incline is too steep, etc.), automatic adjustment of treadmill parameters when the user is too stressed and unable to perform manual adjustment, provide remote alarm activation if the user is hurt (awkward movement, motionless), etc. The system can be used in combination with other body sensors such as heart rate monitor, blood pressure monitor, etc.

During a typical treadmill stress test, a patient may be monitored for ECG and blood pressure measurements using sensors in the chest and arm, respectively. There are several intrinsic limitations with conventional stress testing. The patient's leg or feet movement is typically not monitored. Hence, the walking/running stability of the patent is not monitored. There are inherent safety risks of the patient struggling and falling during several scenarios including but not limited to the following: patient's stride doesn't match the treadmill speed, patient's standing position on the treadmill is incorrect, patient's inability to accelerate walking/running speed during acceleration of the treadmill speed, patient's physical stress or fatigue, medical practitioner operating the treadmill incorrectly, etc.

With the smart shoe interface wirelessly connected to that of the treadmill, the safety risks may be reduced significantly by being able to monitor the patient's physiological and motion state.

Figure 12:
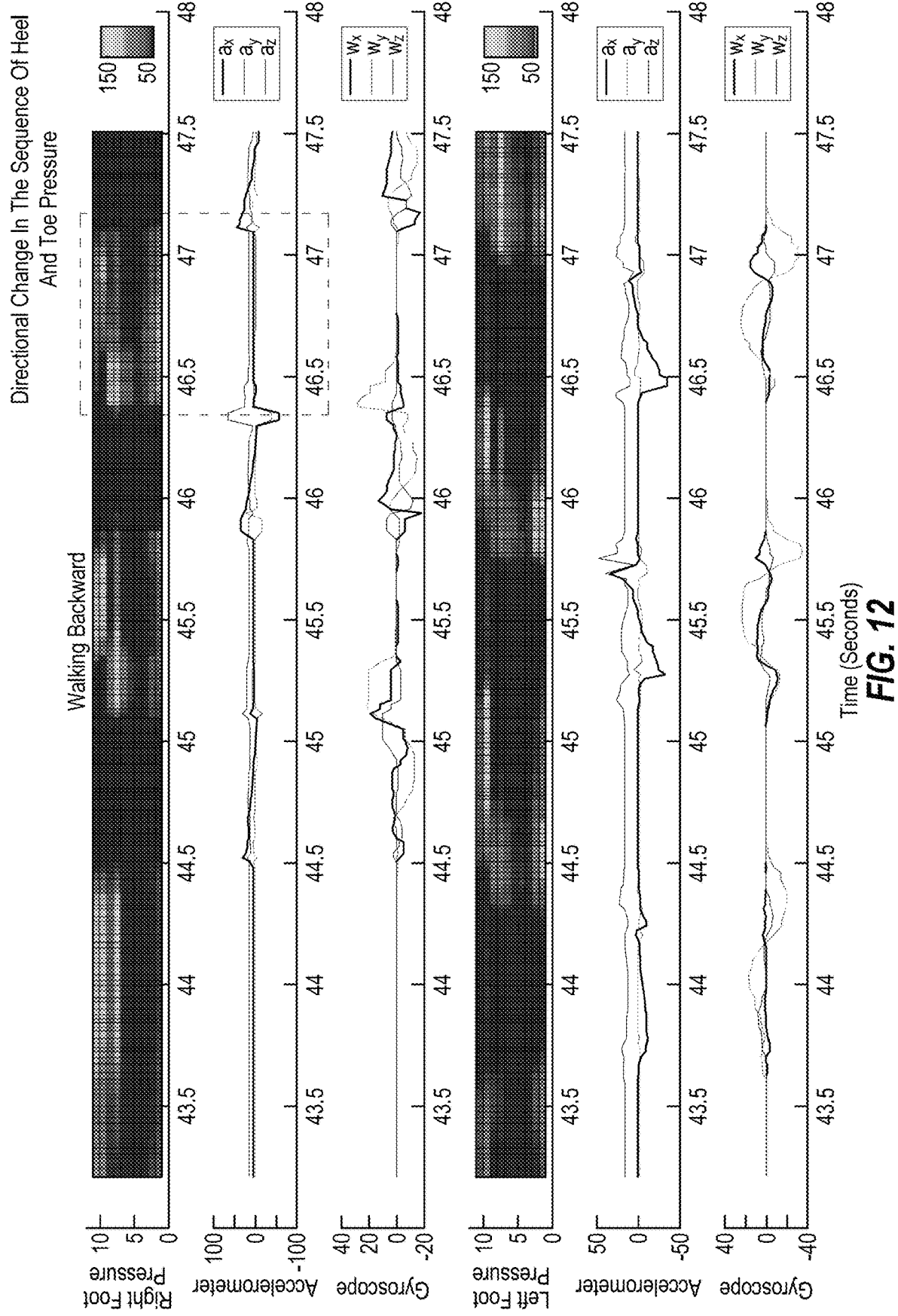
Figure 13:
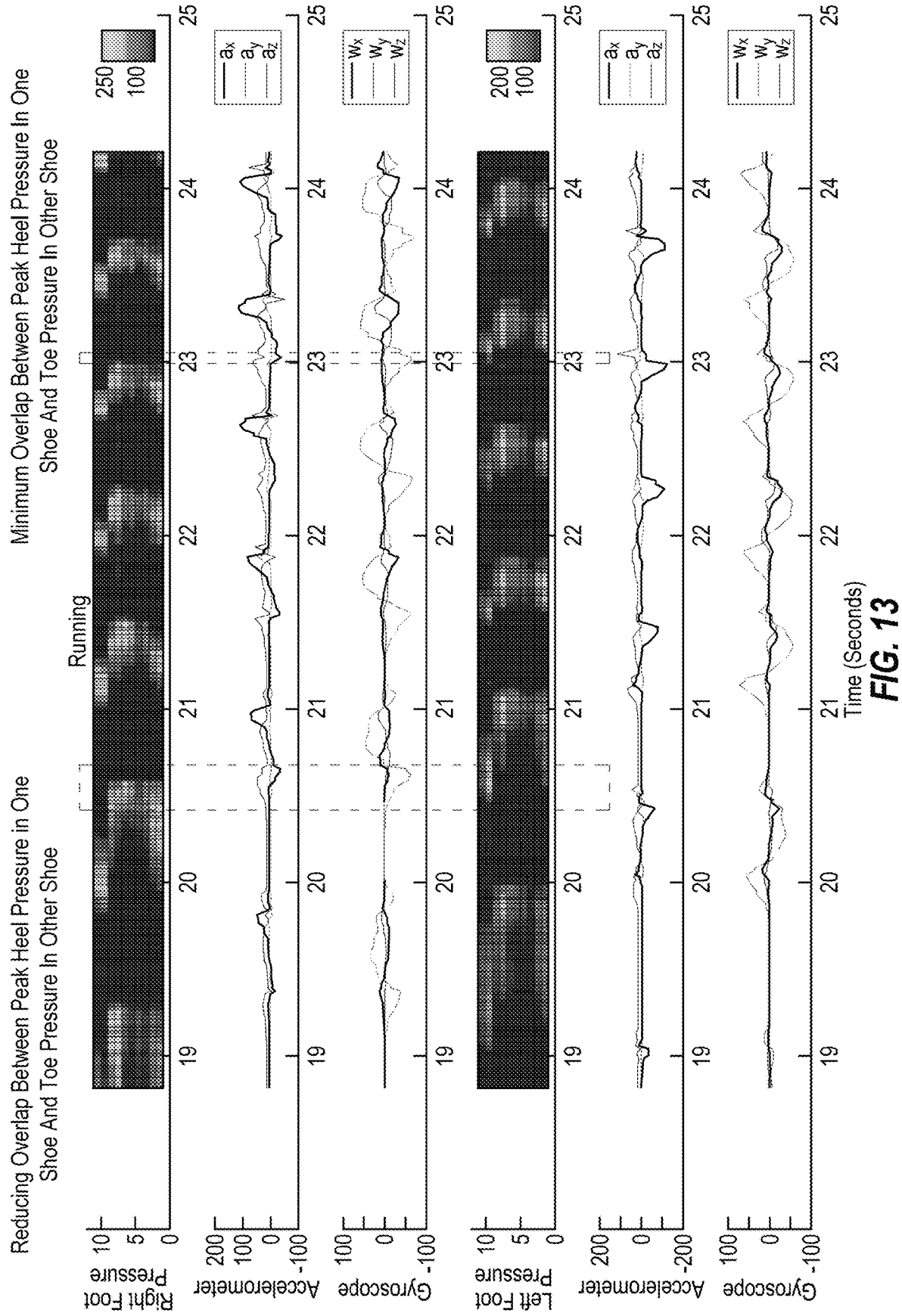
Figure 14:
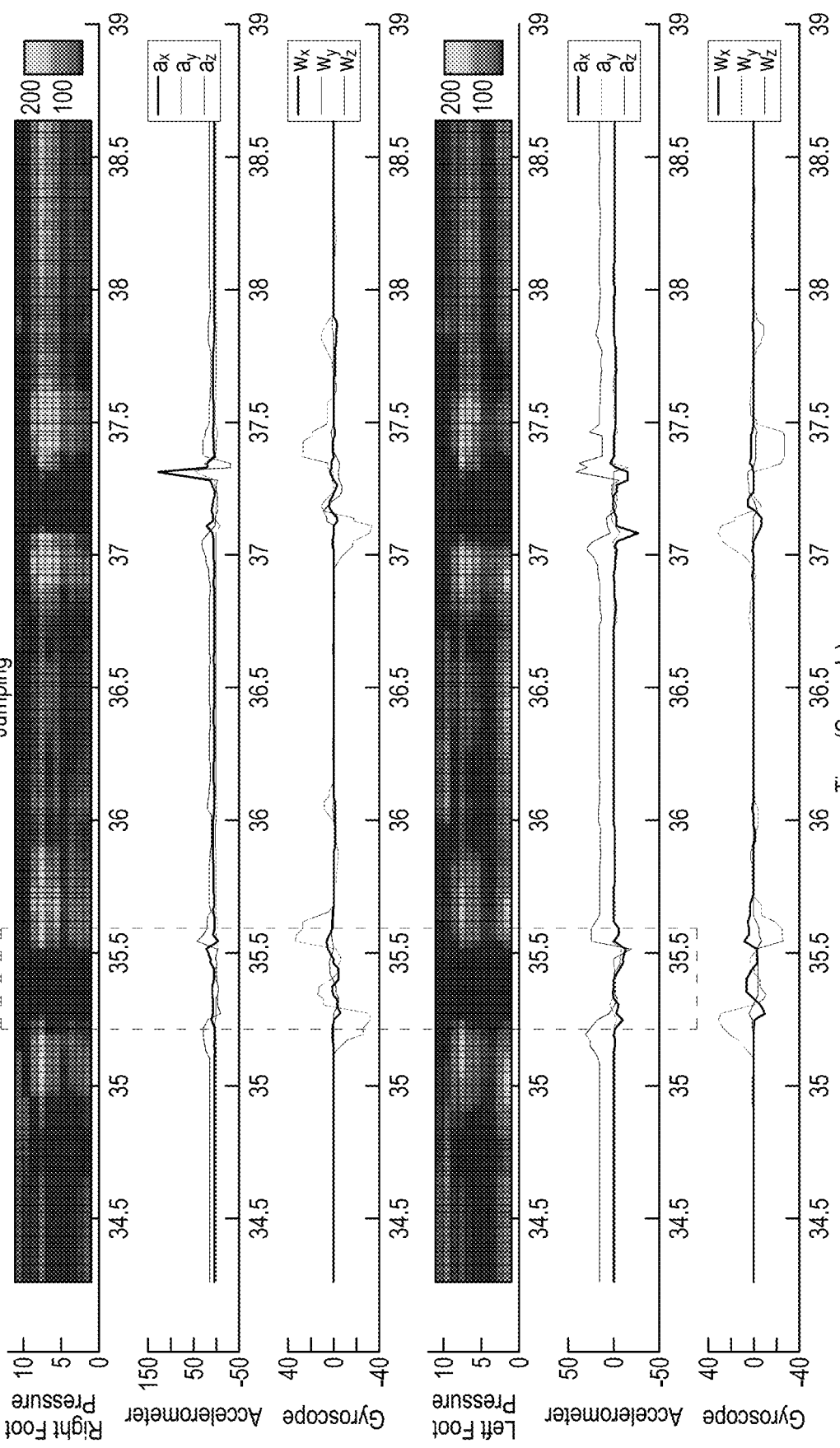

FIGS. 11-21 indicate an example of real-time measurement of monitoring parameters for six defined motion states:
Walking forward (FIG. 11)
Walking backward (FIG. 12)

Figure 15:
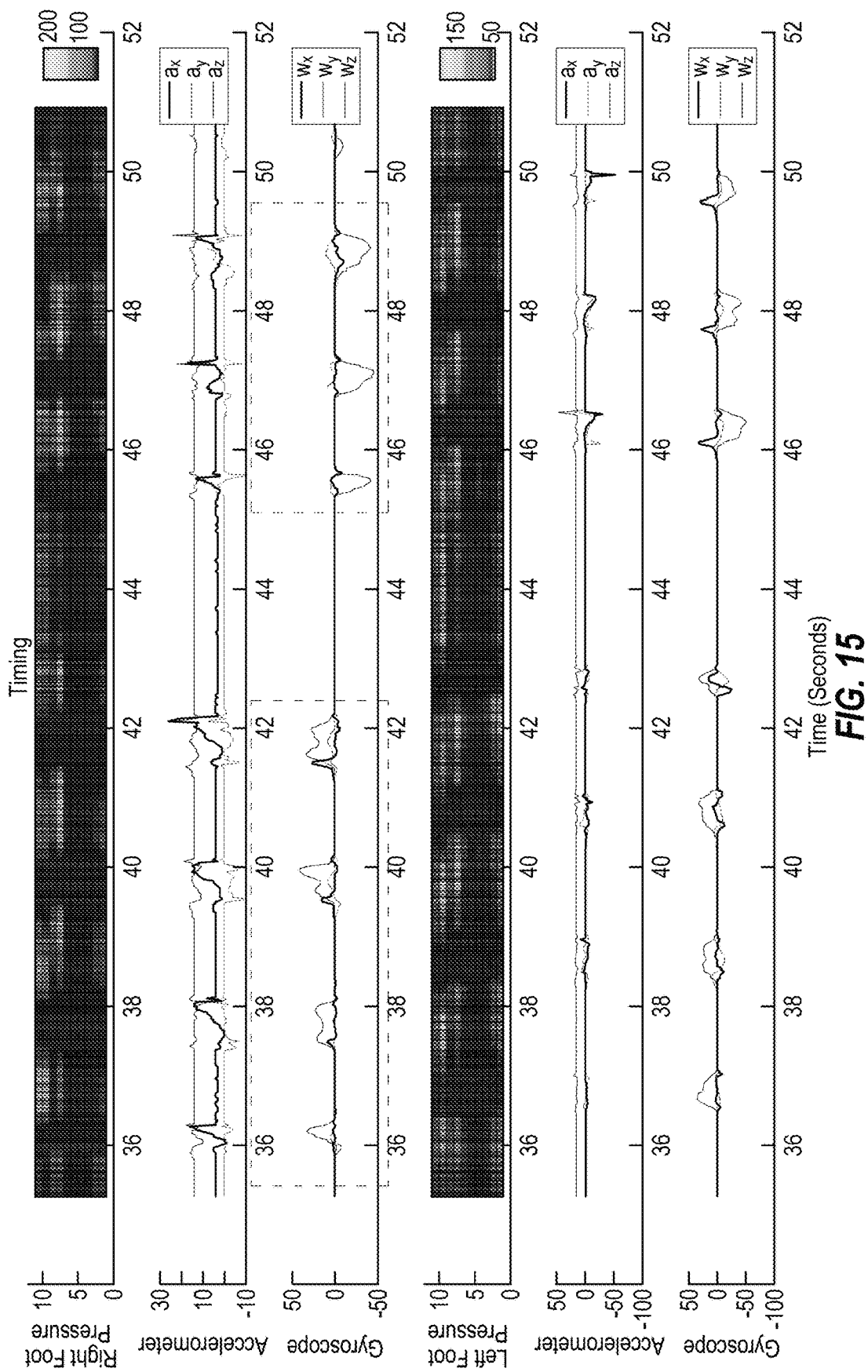
Figure 16:
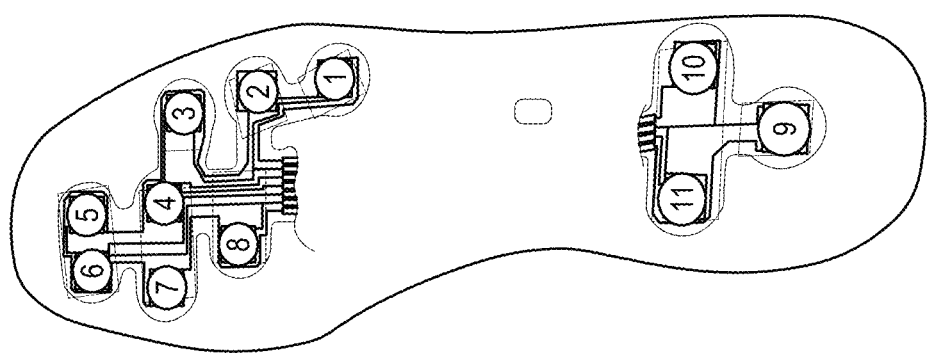
Figure 16:
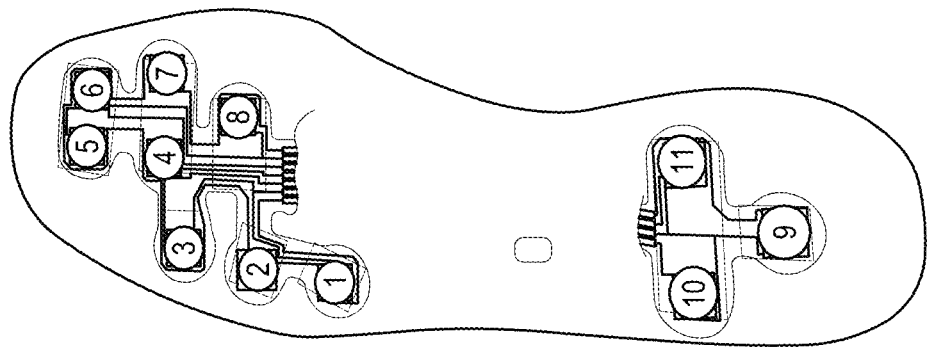
Figure 17:
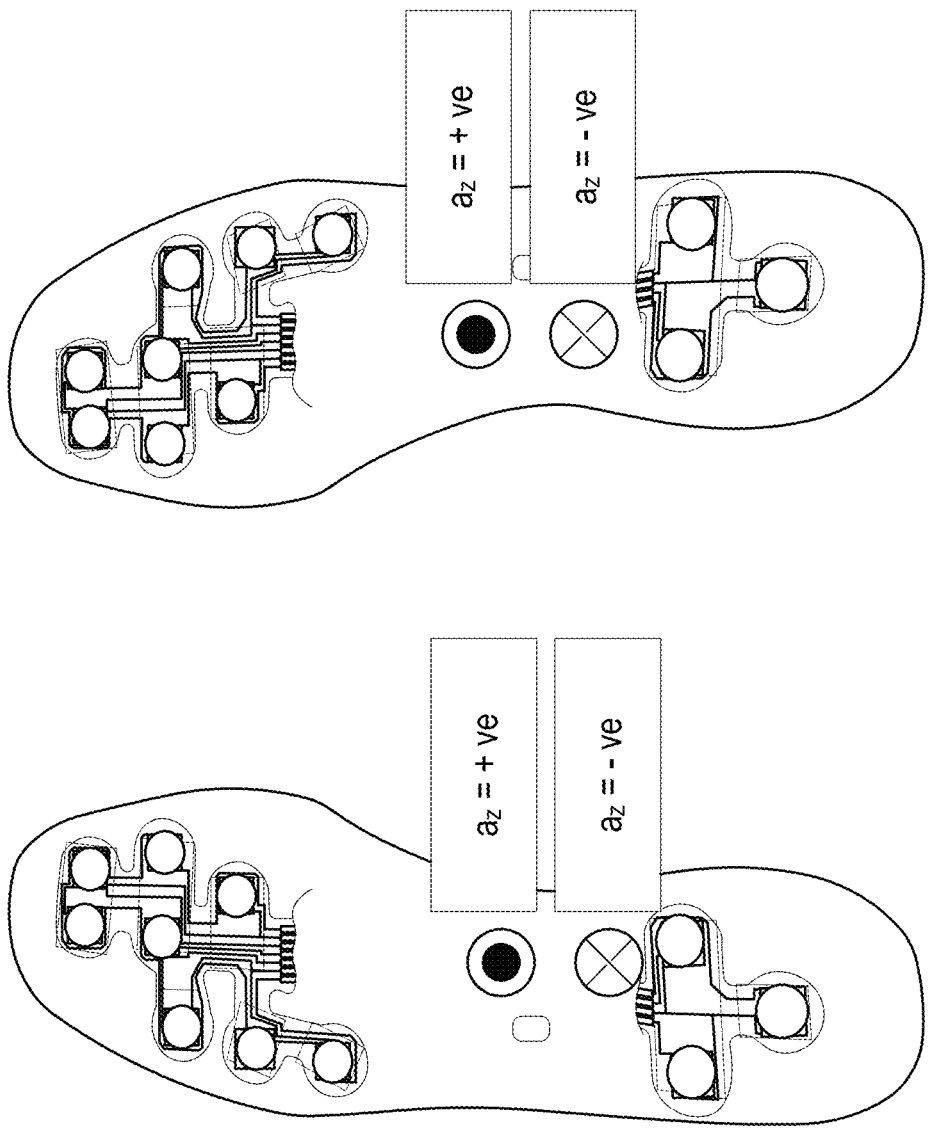
Figure 18:
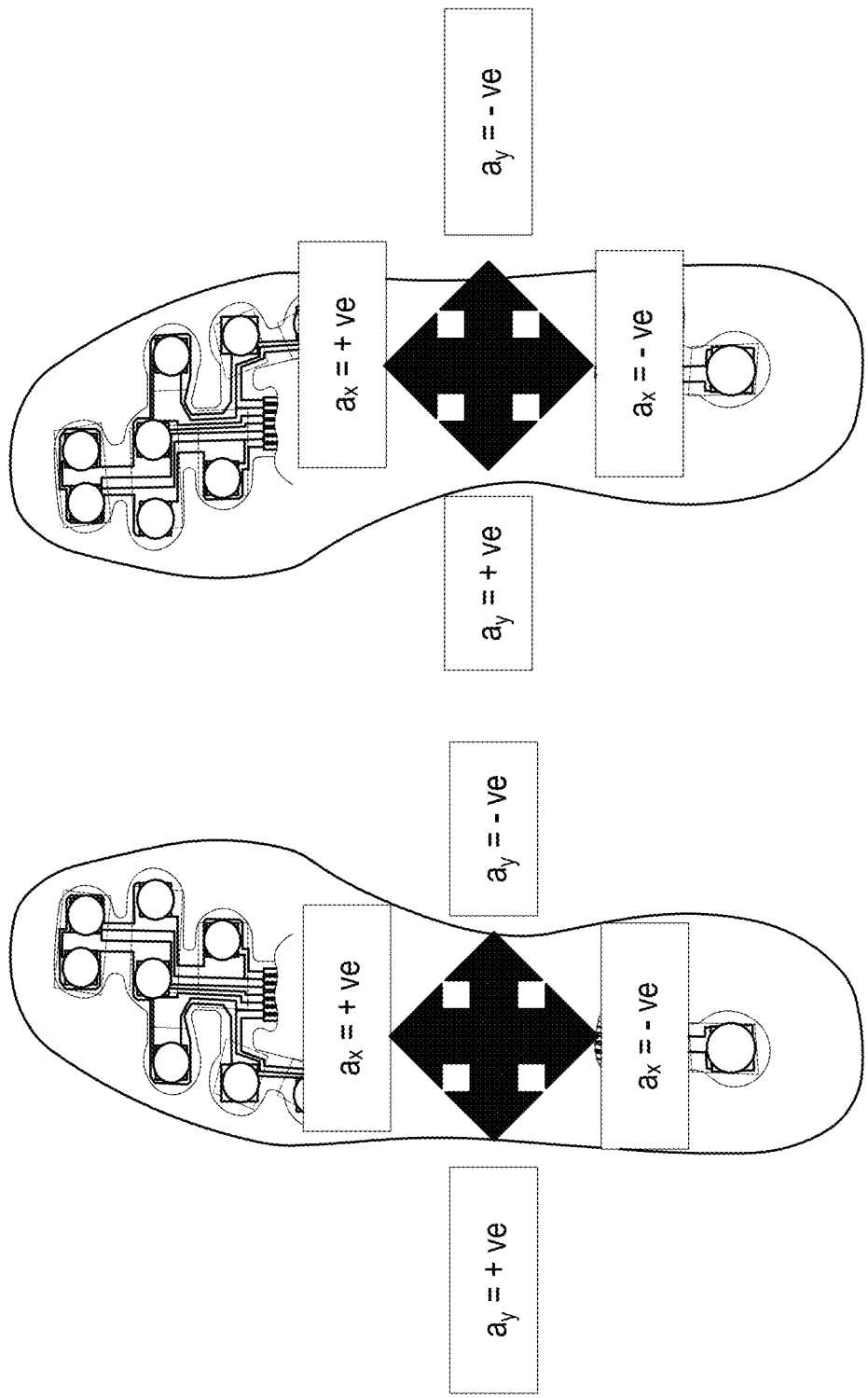
Figure 19:
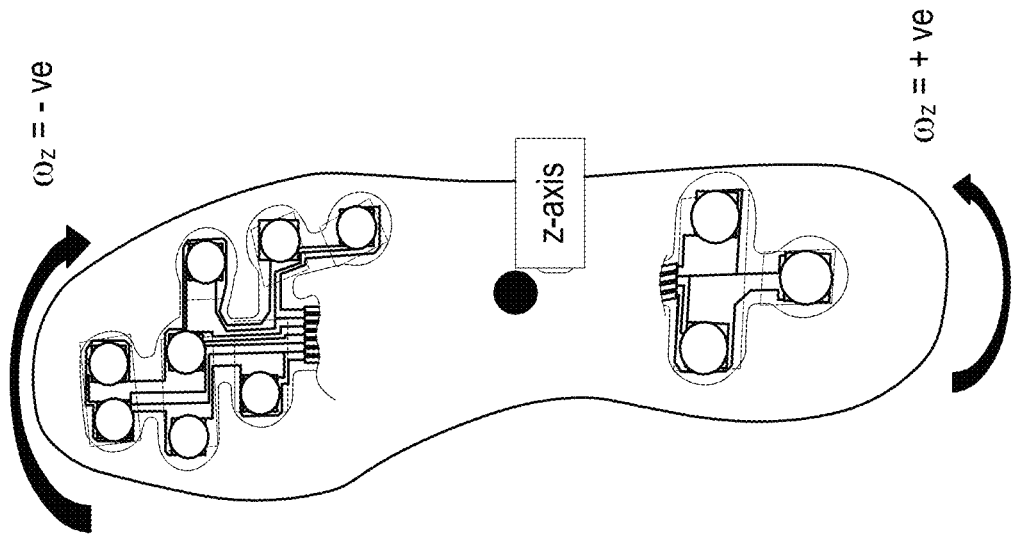
Figure 19:
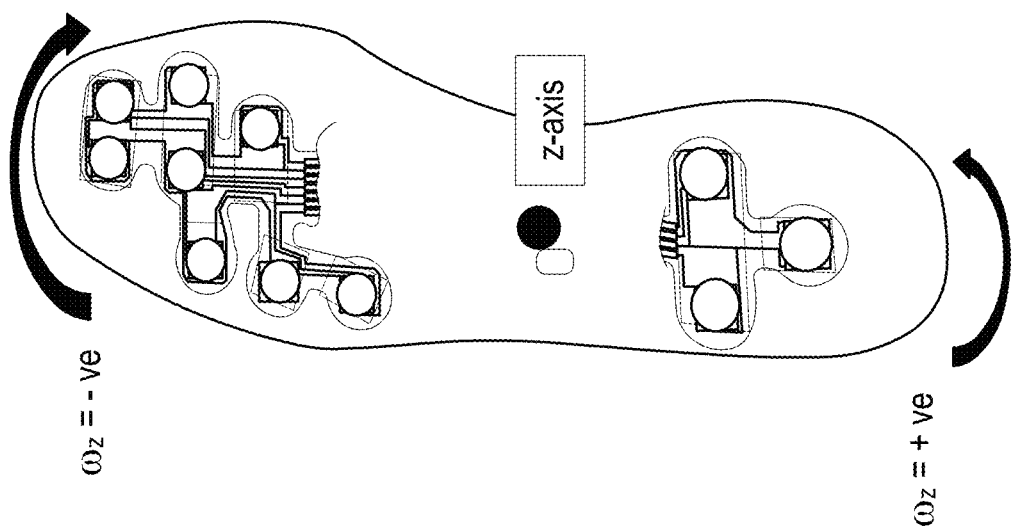
Figure 20:
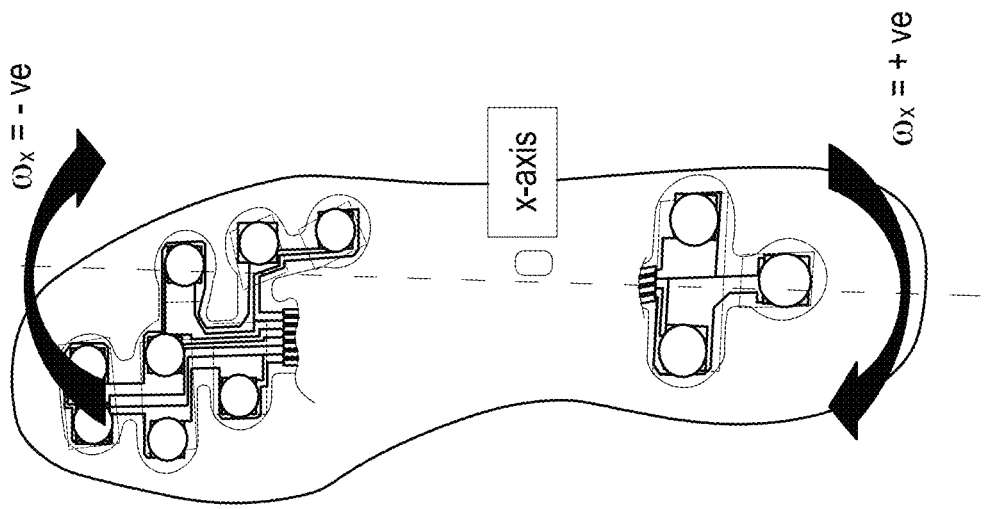
Figure 20:
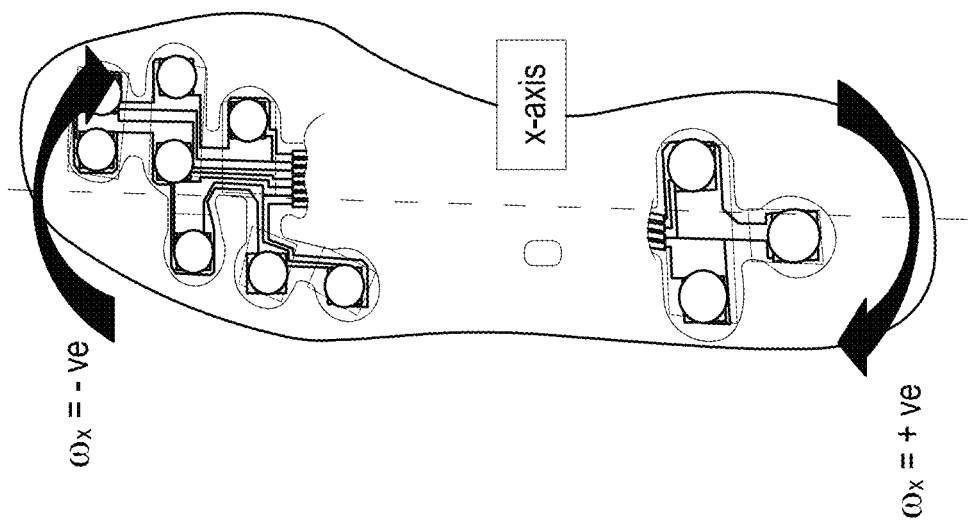
Figure 21:
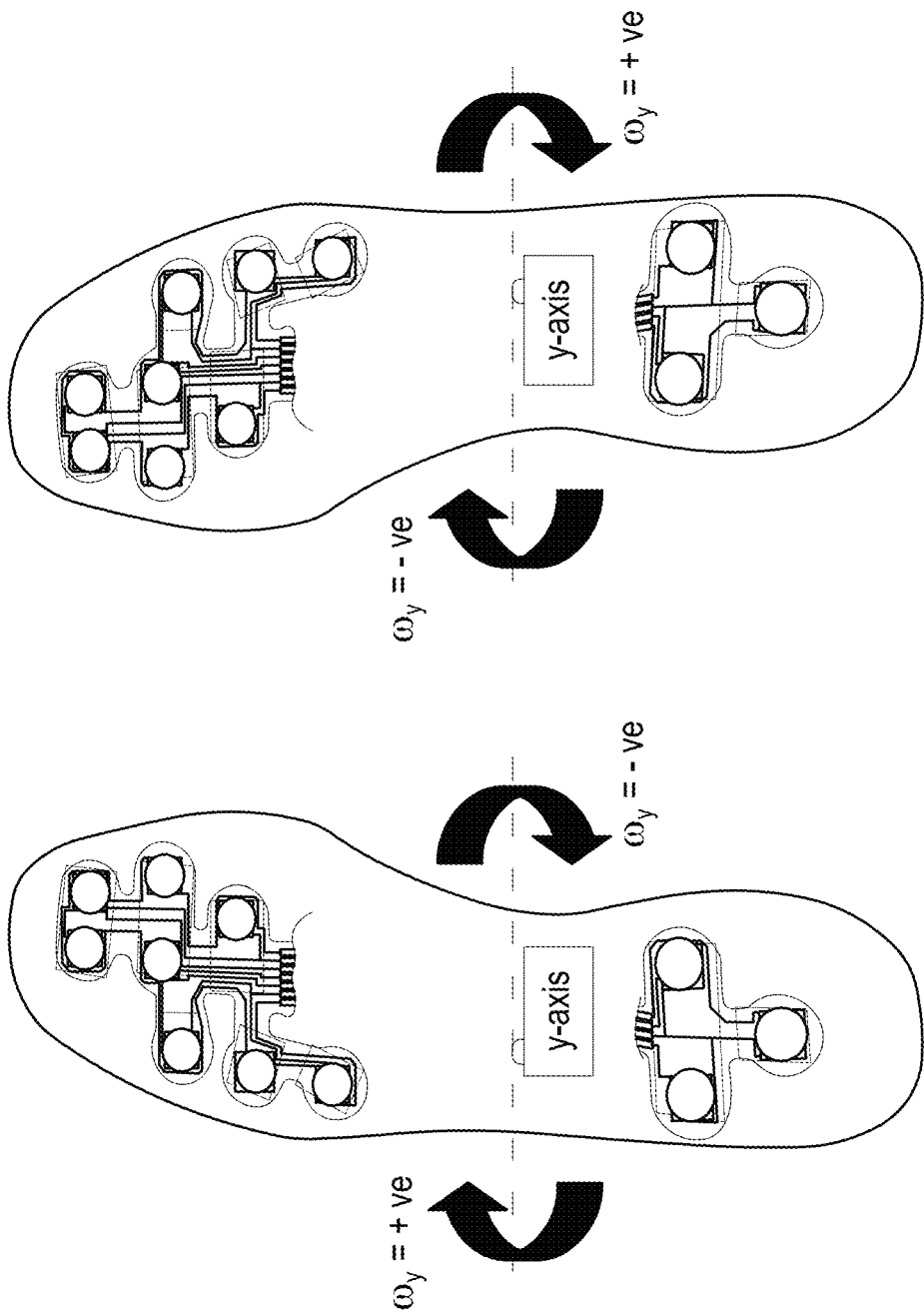

Walking to running transition (FIG. 13)
Jumping (FIG. 14)
Turning (FIG. 15)

Three different types of sensors may be in each shoe insole:
 Force/pressure sensing array (11 sensing nodes, for example, as in FIG. 16)
 3-axis accelerometer (illustrated in FIGS. 17 and 18)
 3-axis gyroscope (illustrated in FIGS. 19 and 21)

"Simplified" identifiers of motion states are indicated in each of the FIGS. 11-21.

Figure 22:
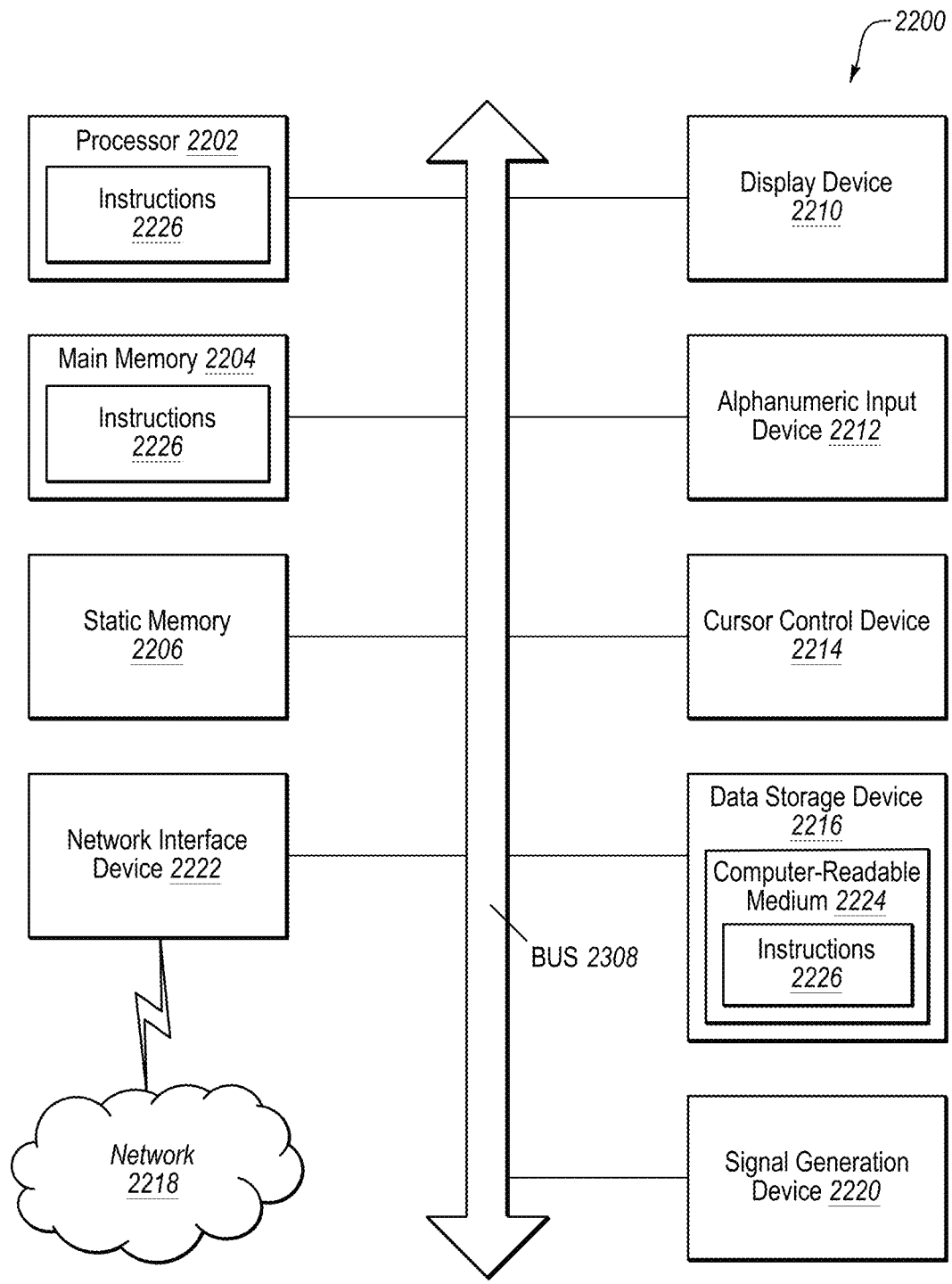
FIG. 22 illustrates a block diagram of an example computer system related to a multi-modal array, according to at least one embodiment of the present disclosure.

FIG. 22 illustrates a block diagram of an example computer system 2200 related to a multi-modal array, according to at least one embodiment of the present disclosure. The host controller described above may be implemented as a computing system such as the example computer system 2200. The computer system 2200 may be configured to implement one or more operations of the present disclosure.

The computer system 2200 executes one or more sets of instructions 2226 that cause the machine to perform any one or more of the methods discussed herein. The machine may operate in the capacity of a server or a client machine in client-server network environment, or as a peer machine in a peer-to-peer (or distributed) network environment. The machine may be a personal computer (PC), a tablet PC, a set-top box (STB), a personal digital assistant (PDA), a mobile telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute the sets of instructions 2226 to perform any one or more of the methods discussed herein.

The computer system 2200 includes a processor 2202, a main memory 2204 (e.g., read-only memory (ROM), flash memory, dynamic random access memory (DRAM) such as synchronous DRAM (SDRAM) or Rambus DRAM (RDRAM), etc.), a static memory 2206 (e.g., flash memory, static random access memory (SRAM), etc.), and a data storage device 2216, which communicate with each other via a bus 2208.

The processor 2202 represents one or more general-purpose processing devices such as a microprocessor, central processing unit, or the like. More particularly, the processor 2202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 2202 may also be one or more special-purpose processing devices such as an application specific integrated circuit (ASIC), a field programmable gate array (FPGA), a digital signal processor (DSP), network processor, or the like. The processor 2202 is configured to execute instructions for performing the operations and steps discussed herein.

The computer system 2200 may further include a network interface device 2222 that provides communication with other machines over a network 2218, such as a local area network (LAN), an intranet, an extranet, or the Internet. The network interface device 2222 may include any number of physical or logical interfaces. The network interface device 2222 may include any device, system, component, or collection of components configured to allow or facilitate communication between network components in a network. For example, the network interface device 2222 may include, without limitation, a modem, a network card (wireless or wired), an infrared communication device, an optical communication device, a wireless communication device (such as an antenna), and/or chipset (such as a Bluetooth device, an 802.xx device (e.g. Metropolitan Area Network (MAN)), a WiFi device, a WiMax device, cellular communication facilities, etc.), and/or the like. The network interface device 2222 may permit data to be exchanged with a network (such as a cellular network, a WiFi network, a MAN, an optical network, etc., to name a few examples) and/or any other devices described in the present disclosure, including remote devices. In at least one embodiment, the network interface device 2222 may be logical distinctions on a single physical component, for example, multiple communication streams across a single physical cable or optical signal.

The computer system 2200 also may include a display device 2210 (e.g., a liquid crystal display (LCD) or a cathode ray tube (CRT)), an alphanumeric input device 2212 (e.g., a keyboard), a cursor control device 2214 (e.g., a mouse), and a signal generation device 2220 (e.g., a speaker).

The data storage device 2216 may include a computer-readable storage medium 2224 on which is stored the sets of instructions 2226 embodying any one or more of the methods or functions described herein. The sets of instructions 2226 may also reside, completely or at least partially, within the main memory 2204 and/or within the processor 2202 during execution thereof by the computer system 2200, the main memory 2204 and the processor 2202 also constituting computer-readable storage media. The sets of instructions 2226 may further be transmitted or received over the network 2218 via the network interface device 2222.

While the example of the computer-readable storage medium 2224 is shown as a single medium, the term "computer-readable storage medium" may include a single medium or multiple media (e.g., a centralized or distributed database, and/or associated caches and servers) that store the sets of instructions 2226. The term "computer-readable storage medium" may include any medium that is capable of storing, encoding or carrying a set of instructions for execution by the machine and that cause the machine to perform any one or more of the methods of the present disclosure. The term "computer-readable storage medium" may include, but not be limited to, solid-state memories, optical media, and magnetic media.

Modifications, additions, or omissions may be made to the computer system 2200 without departing from the scope of the present disclosure. For example, in at least one embodiment, the computer system 2200 may include any number of other components that may not be explicitly illustrated or described.

As used in the present disclosure, the terms "module" or "component" may refer to specific hardware implementations configured to perform the actions of the module or component and/or software objects or software routines that may be stored on and/or executed by general purpose hardware (e.g., computer-readable media, processing devices, etc.) of the computing system. In at least one embodiment, the different components, modules, engines, and services described in the present disclosure may be implemented as objects or processes that execute on the computing system (e.g., as separate threads). While some of the system and methods described in the present disclosure are generally described as being implemented in software (stored on and/or executed by general purpose hardware), specific hardware implementations or a combination of software and specific hardware implementations are also possible and contemplated. In the present disclosure, a "computing entity" may be any computing system as previously defined in the present disclosure, or any module or combination of modulates running on a computing system.

Terms used in the present disclosure and especially in the appended claims (e.g., bodies of the appended claims) are generally intended as "open" terms (e.g., the term "including" may be interpreted as "including, but not limited to," the term "having" may be interpreted as "having at least," the term "includes" may be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases may not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" may be interpreted to mean "at least one" or "one or more"); the same holds true for the use of definite articles used to introduce claim recitations.

In addition, even if a specific number of an introduced claim recitation is explicitly recited, those skilled in the art will recognize that such recitation may be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, may be understood to contemplate the possibilities of including one of the terms, either of the terms, or both terms. For example, the phrase "A or B" may be understood to include the possibilities of "A" or "B" or "A and B."

All examples and conditional language recited in the present disclosure are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, various changes, substitutions, and alterations may be made hereto without departing from the spirit and scope of the present disclosure.

What is claimed is:

1. An insole system, comprising:
   a first insole of a first wearable foot device for a first foot of a user, the first insole including a plurality of first force sensors configured to generate first force data;
   a second insole of a second wearable foot device for a second foot of the user, the second insole including a plurality of second force sensors configured to generate second force data;
   a host controller; and
   a communications interface configured to couple the plurality of first force sensors and the plurality of second force sensors with the host controller,
   wherein the host controller is configured to determine a type of an activity of the user of the first wearable foot device based on a correlation between the first force data and the second force data, including an amount of overlap between an occurrence of pressure in a first portion of the first insole and an occurrence of pressure in a second portion of the second insole, the first portion being different than the second portion,
   wherein one or more characteristics of two or more of the plurality of first force sensors are customized based on locations of the two or more of the plurality of first force sensors within the first insole so that one of the plurality of first force sensors is customized with different characteristics than another of the plurality of first force sensors,
   wherein the first force data is obtained from a scan of the plurality of first force sensors, and a first set of the plurality of first force sensors is scanned at a first rate and a second set of the plurality of first force sensors is scanned at a second rate different than the first rate,
   wherein the first rate scanning is selected based on locations of the first set of the plurality of first force sensors and the second rate of scanning is selected based on locations of the second set of the plurality of first force sensors,
   wherein the first insole further includes a first accelerometer sensor configured to generate first accelerometer data, the second insole further includes a second accelerometer sensor configured to generate second accelerometer data, and the type of the activity is determined based on a correlation between the first force data, the first accelerometer data, the second force data, and the second accelerometer data, including a peak of the first accelerometer data occurring before a peak of the first force data from the first portion of the first insole.

2. The insole system of claim 1, wherein the first insole includes an environmental sensor that is positioned in a first location of the first wearable foot device that receives lower levels of force or bending applied by a first foot in the first wearable foot device than a second location of the first wearable foot device where one or more of the plurality of first force sensors are positioned.

3. A method, comprising:
   receiving, by a processor, first data from a first insole of a first wearable foot device for a first foot of a user, wherein the first data includes:
      first force data from a plurality of force sensors included in a first sensing layer in the first insole, the plurality of force sensors configured to generate the first force data, wherein one or more characteristics of two or more of the plurality of force sensors are customized based on locations of the two or more of the plurality of force sensors within the first insole so that one of the plurality of force sensors is customized with different characteristics than another of the plurality of force sensors; and
      first accelerometer data from a first accelerometer sensor included in the first insole; and
   determining, by the processor, a type of an activity of the user based on a correlation between the first force data and the first accelerometer data, wherein the type of the activity is determined based on a peak of the first accelerometer data occurring before a peak of the first force data from a portion of the first insole.

4. The method of claim 3, further comprising:
determining a live graphical display based on the activity; and
providing the live graphical display via a graphical user interface.

5. The method of claim 4, wherein the live graphical display includes a three-dimensional pressure map.

6. The method of claim 3, wherein the one or more characteristics include a force range, a rise time, and a fall time.

7. The method of claim 3, further comprising:
identifying environmental parameters that contribute noise to the first data from an environmental sensor, wherein the environmental sensor is positioned in a first location of the first wearable foot device that receives lower levels of force applied by a foot in the first wearable foot device than a second location of the first wearable foot device where one or more of the plurality of force sensors are positioned; and
adjusting the first data to account for the environmental parameters to reduce the noise in the first data.

8. The method of claim 3, further comprising in response to the first data, determine, by the processor, instructions for generation of feedback for the user, the feedback being configured to be felt by the user.

9. A shoe system, comprising:
a first insole that includes a first sensing layer, the first sensing layer including
a plurality of force sensors configured to generate force data, wherein one or more characteristics of two or more of the plurality of force sensors are customized based on locations of the two or more of the plurality of force sensors within the first insole so that one of the plurality of force sensors is customized with different characteristics than another of the plurality of force sensors; and
an accelerometer sensor configured to generate accelerometer data; and
a communications interface configured to direct the force data and the accelerometer data to a host controller configured to determine a type of an activity of a user of the shoe system based on a correlation between the force data and the accelerometer data, wherein the type of the activity is determined based on a peak of the accelerometer data occurring before a peak of the force data from a portion of the first insole.

10. The shoe system of claim 9, wherein the first insole is included in a first wearable foot device for a first foot of the user, the shoe system further comprising a second insole of a second wearable foot device for a second foot of the user, the second insole including:
a second force sensor configured to generate second force data; and
a second accelerometer sensor configured to generate second accelerometer data,
wherein the type of activity of the user is determined based on a correlation between the force data, the accelerometer data, the second force data, and the second accelerometer data, including an amount of overlap between an occurrence of pressure in a first portion of the first insole and an occurrence of pressure in a second portion of the second insole, where the first portion is different than the second portion.

11. The shoe system of claim 9, wherein the activity is at least one of: walking, running, jumping, or turning.

* * * * *